US011293932B2

(12) United States Patent
Cummins et al.

(10) Patent No.: US 11,293,932 B2
(45) Date of Patent: *Apr. 5, 2022

(54) MULTIPLEXED DIAGNOSTIC TO RECOGNIZE CONCENTRATIONS OF RELATED PROTEINS AND PEPTIDES

(71) Applicant: North Carolina State University, Raleigh, NC (US)

(72) Inventors: Brian Michael Cummins, Raleigh, NC (US); Frances Smith Ligler, Raleigh, NC (US); Glenn Walker, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 103 days.

This patent is subject to a terminal disclaimer.

(21) Appl. No.: 16/723,402

(22) Filed: Dec. 20, 2019

(65) Prior Publication Data

US 2020/0200772 A1    Jun. 25, 2020

Related U.S. Application Data

(63) Continuation of application No. 14/979,946, filed on Dec. 28, 2015, now Pat. No. 10,545,158.

(60) Provisional application No. 62/097,252, filed on Dec. 29, 2014.

(51) Int. Cl.
| | | |
|---|---|---|
| *G01N 33/53* | (2006.01) | |
| *G01N 33/74* | (2006.01) | |
| *G01N 33/566* | (2006.01) | |
| *G01N 33/68* | (2006.01) | |

(52) U.S. Cl.
CPC ......... *G01N 33/74* (2013.01); *G01N 33/566* (2013.01); *G01N 33/6845* (2013.01); *G01N 2333/635* (2013.01)

(58) Field of Classification Search
None
See application file for complete search history.

(56) References Cited

U.S. PATENT DOCUMENTS

| | | | |
|---|---|---|---|
| 4,508,828 A | 4/1985 | Lindall et al. | |
| 6,329,209 B1 | 12/2001 | Wagner et al. | |
| 6,689,566 B1 | 2/2004 | Cantor et al. | |
| 6,743,590 B1 | 6/2004 | Cantor et al. | |
| 7,575,720 B2 | 8/2009 | Novak et al. | |
| 8,004,685 B2 | 8/2011 | Yamamichi et al. | |
| 8,329,409 B2 * | 12/2012 | Cantor | G01N 33/78 435/7.1 |
| 8,455,212 B2 | 6/2013 | Konrath et al. | |
| 9,377,473 B2 | 6/2016 | Lavigne et al. | |
| 10,545,158 B2 * | 1/2020 | Cummins | G01N 33/74 |
| 2003/0143580 A1 | 7/2003 | Straus et al. | |
| 2005/0250141 A1 | 11/2005 | Lambert et al. | |
| 2006/0110739 A1 | 5/2006 | Heyduk et al. | |
| 2009/0197284 A1 | 8/2009 | Kiernan et al. | |
| 2011/0117670 A1 | 5/2011 | Walker et al. | |
| 2013/0217058 A1 | 8/2013 | Lopez et al. | |
| 2013/0217630 A1 | 8/2013 | Nelson et al. | |
| 2016/0195552 A1 | 7/2016 | Cummins et al. | |

FOREIGN PATENT DOCUMENTS

WO    WO 2016/109378 A1    7/2016

OTHER PUBLICATIONS

Bieglmayer et al., "Kinetic analyses of parathyroid hormone clearance as measured by three rapid immunoassays during parathyroidectomy," Clinical Chemistry 48:10, pp. 1731-1738 (2002).
Boudou et al., "Third-or second-generation parathyroid hormone assays: A remaining debate in the diagnosis of primary hyperparathyroidism," Journal of Clinical Endocrinology and Metabolism 90(12), pp. 6370-6372 (2005).
Carneiro et al., "Comparison of intraoperative iPTH assay (QPTH) criteria in guiding parathyroidectomy: Which criterion is the most accurate?" Surgery 134(6), pp. 973-979 (Dec. 2003).
Caron et al., "High third generation/second generation PTH ratio in a patient with parathyroid carcinoma: Clinical utility of third generation/second generation PTH ratio in patients with primary hyperparathyroidism." Clinical Endocrinology 70(4), pp. 533-538 (2009).
Cavalier et al., "The third/second generation PTH assay ratio as a marker for parathyroid carcinoma: Evaluation using an automated platform," Journal of Clinical Endocrinology and Metabolism 99(3), pp. E453-E457 (Mar. 2014).
Gao et al., "Evolution of the Parathyroid Hormone (PTH) Assay—Importance of Circulating PTH Immunoheterogeneity and of its Regulation." Clinical Laboratory, 51(1-2), pp. 21-29 (2005).
Goodman, "The evolution of assays for parathyroid hormone." Seminars in Dialysis, 18(4), 296-301 (2005).

(Continued)

*Primary Examiner* — Gary Counts
(74) *Attorney, Agent, or Firm* — Jenkins, Wilson, Taylor & Hunt, P.A.

(57) ABSTRACT

Disclosed are methods and systems for determining concentrations of a target molecule and a variant thereof in a sample. The sample can comprise or be suspected to comprise a target molecule and at least one variant thereof and is exposed to one or more recognition elements that bind to the target molecule and/or the at least one variant. A signal is detected that is associated with the binding of the target molecule and/or a signal is detected that is associated with the binding of the at least one variant to the one or more recognition elements. The concentration of the target molecule and/or the at least one variant thereof is determined based on the signals. The system can comprise a receiver adapted to receive a sample comprising or suspected to comprise a target molecule and the at least one variant thereof, the receiver comprising one or more recognition elements that bind to one or more epitopes in the target molecule and/or the at least one variant thereof.

11 Claims, 12 Drawing Sheets

Specification includes a Sequence Listing.

(56) References Cited

OTHER PUBLICATIONS

Grant et al., "Primary Hyperparathyroidism Surgical Management Since the Introduction of Minimally Invasice Parathyroidectomy," Arch Surg., Mayo Clinic Experience, 140(5), pp. 472-479 (2005).
Greene et al., "National Trends in Parathyroid Surgery from 1998 to 2008: A Decade of Change," J Am Col of Surg., 209(3), pp. 332-343 (May 29, 2009).
International Preliminary Report on Patentability for International Patent Application PCT/US2015/067575 dated Jul. 4, 2017.
Inabnet, "Intraoperative Parathyroid Hormone Monitoring", World J Surg., vol. 28(12), pp. 1212-1215 (Dec. 2004).
Interview Summary corresponding to U.S. Appl. No. 14/979,946 dated Jun. 25, 2018.
Larsson, "Generation and characterization of antibodies for proteomics research," Royal Institute of Technology, School of Biotechnology, Stockholm, pp. 1-14 (2009).
Lass-Napiorkowska et al., "Detection methodolgy based on target molecule induced sequence specific binding to a single stranded oligonucleotide," Anal. Chem., vol. 84, pp. 3382-3389 (Mar. 2012).
Ligler et al., "The array biosensor: Portable, automated systems," Anal. Sci. 23, pp. 5-10 (2007).
Lochhead et al. "Rapid Multiplexed Immunoassay for Simultaneous Serodiagnosis of HIV-1 and Coinfections," J. Clin.Micro., vol. 49(10), pp. 3584-35900 (Oct. 2011).
Meneely et al., "Development and Validation of an Ultrasensitive Fluorescence Planar Waveguide Biosensor for the Detection of Paralytic Shellfish Toxins in Marine Algae," Biosensors and Bioelectronics. 41, pp. 691-697 (2013).
Meyer et al., "Clinical impact of two different intraoperative parathyroid hormone assays in primary and renal hyperparathyroidism," Eur J Endocrinol. Feb. 2009; 160(2), pp. 275-281 (2009).
Nguyen-Yamamoto et al., "Origin of parathyroid hormone (PTH) fragments detected by intact-PTH assays," European Journal of Endocrinology 147(1), pp. 123-131 (2002).
Notification of Transmittal of the International Search Report and the Written Opinion of the International Searching Authority, or the Declaration for International Application No. PCT/US15/67575 dated Apr. 1, 2016.
Notice of Allowance and Interview Summary corresponding to U.S. Appl. No. 14/979,946 dated Sep. 13, 2019.
Office Action (Restriction Requirement) corresponding to U.S. Appl. No. 14/979,946 dated Oct. 20, 2017.
Office Action corresponding to U.S. Appl. No. 14/979,946 dated Mar. 28, 2018.
Office Action corresponding to U.S. Appl. No. 14/979,946 dated Oct. 26, 2018.
Office Action corresponding to U.S. Appl. No. 14/979,946 dated Mar. 11, 2019.
Potts, "A Short History of Parathyroid Hormone, Its Biological Role, and Pathophysiology of Hormone Excess." Journal of Clinical Densitometry, vol. 16(1), pp. 4-7 (2013).
Strojan et al., "Contemporary management of lymph node metastases from an unknown primary to the neck: I. A review of diagnostic approaches," Clinical review, Head & Neck, pp. 123-132 (Jan. 2013).
Udelsman, "Six Hundred Fifty-Six Consecutive Explorations for Primary Hyperparathyroidism," Annals of Surgery, vol. 235, No. 5, pp. 665-672 (2002).
Yamashita et al. "Large carboxy-terminal parathyroid hormone (PTH) fragment with a relatively longer half-life than 1-84 PTH is secreted directly from the parathyroid gland in humans," European Journal of Endocrinology 149(4) pp. 301-306 (2003).
Irvin III et al., "Operative Monitoring of Parathyroid Gland Hyperfunction," Am J Surg., vol. 162, No. 4, pp. 299-302 (1991).
Irvin III et al., "Clinical Usefulness of an Intraoperative 'Quick Parathyroid Hormone' Assay," and discussion, Surgery, vol. 114, No. 6, pp. 1019-1023 (1993).

* cited by examiner

SEQUENCE LISTING

```
<160> NUMBER OF SEQ ID NOS: 7

<210> SEQ ID NO 1
<211> LENGTH: 84
<212> TYPE: PRT
<213> ORGANISM: Homo sapiens

<400> SEQUENCE: 1

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys Lys Glu Asp Asn Val Leu Val Glu Ser His Glu
    50                  55                  60

Lys Ser Leu Gly Glu Ala Asp Lys Ala Asp Val Asn Val Leu Thr Lys
65                  70                  75                  80

Ala Lys Ser Gln

<210> SEQ ID NO 2
<211> LENGTH: 78
<212> TYPE: PRT
<213> ORGANISM: Homo sapiens

<400> SEQUENCE: 2

Leu Met His Asn Leu Gly Lys His Leu Asn Ser Met Glu Arg Val Glu
1               5                   10                  15
```

```
Trp Leu Arg Lys Lys Leu Gln Asp Val His Asn Phe Val Ala Leu Gly
             20                  25                  30

Ala Pro Leu Ala Pro Arg Asp Ala Gly Ser Gln Arg Pro Arg Lys Lys
         35                  40                  45

Glu Asp Asn Val Leu Val Glu Ser His Glu Lys Ser Leu Gly Glu Ala
 50                  55                  60

Asp Lys Ala Asp Val Asn Val Leu Thr Lys Ala Lys Ser Gln
 65                  70                  75
```

<210> SEQ ID NO 3
<211> LENGTH: 6
<212> TYPE: PRT
<213> ORGANISM: Homo sapiens

<400> SEQUENCE: 3

```
Ser Val Ser Glu Ile Gln
 1               5
```

<210> SEQ ID NO 4
<211> LENGTH: 11
<212> TYPE: PRT
<213> ORGANISM: Homo sapiens

<400> SEQUENCE: 4

```
Leu Asn Ser Met Glu Arg Val Glu Trp Leu Arg
 1               5                  10
```

<210> SEQ ID NO 5
<211> LENGTH: 32
<212> TYPE: PRT
<213> ORGANISM: Homo sapiens

<400> SEQUENCE: 5

```
Lys Lys Glu Asp Asn Val Leu Val Glu Ser His Glu Lys Ser Leu Gly
 1               5                  10                  15

Glu Ala Asp Lys Ala Asp Val Asn Val Leu Thr Lys Ala Lys Ser Gln
             20                  25                  30
```

<210> SEQ ID NO 6
<211> LENGTH: 85
<212> TYPE: PRT
<213> ORGANISM: Homo sapiens

<400> SEQUENCE: 6

```
Met Ser Val Ser Glu Ile Gln Leu Met His Asn Leu Gly Lys His Leu
 1               5                  10                  15

Asn Ser Met Glu Arg Val Glu Trp Leu Arg Lys Lys Leu Gln Asp Val
             20                  25                  30

His Asn Phe Val Ala Leu Gly Ala Pro Leu Ala Pro Arg Asp Ala Gly
         35                  40                  45

Ser Gln Arg Pro Arg Lys Lys Glu Asp Asn Val Leu Val Glu Ser His
 50                  55                  60

Glu Lys Ser Leu Gly Glu Ala Asp Lys Ala Asp Val Asn Val Leu Thr
 65                  70                  75                  80

Lys Ala Lys Ser Gln
                 85
```

<210> SEQ ID NO 7
<211> LENGTH: 10
<212> TYPE: PRT

```
<213> ORGANISM: Homo sapiens

<400> SEQUENCE: 7

Ser Val Ser Glu Ile Gln Leu Met His Asn
1               5                   10
```

MULTIPLEXED DIAGNOSTIC TO RECOGNIZE CONCENTRATIONS OF RELATED PROTEINS AND PEPTIDES

RELATED APPLICATIONS

This application is a continuation of U.S. patent application Ser. No. 14/979,946, filed Dec. 28, 2015, now U.S. Pat. No. 10,545,158, which claims priority to and the benefit of U.S. Provisional Patent Application No. 62/097,252, filed Dec. 29, 2014, the disclosures of each of which are incorporated herein by reference in their entireties.

STATEMENT OF GOVERNMENT SUPPORT

This invention was made with government support under grant number TR001111 awarded by the National Institutes of Health (NIH). The government has certain rights to this invention.

TECHNICAL FIELD

The presently disclosed subject matter relates to multiplexed systems and related methods that can be used to determine concentrations of target molecules and variants thereof in a sample, for example, to better diagnose disorders, such as endocrinological disorders.

BACKGROUND

Certain endocrinological disorders are currently diagnosed via traditional in vitro diagnostic tests that employ sandwich immunoassays in an effort to achieve the desired selectivity and sensitivity for the hormone of interest. However, the peripheral metabolism of whole hormone into fragments and the relative clearance of whole hormone and hormone fragments vary widely from person to person and create a complex mixture to be measured. Depending on the diagnostic test that is chosen (and the corresponding recognition elements of that test), there can be significantly different test results for the desired protein of interest, using the same calibration standards. In addition, a better understanding of the relative populations of a protein and its fragments and the underlying kinetics of metabolism of the protein can potentially provide important information for more effective understanding and treatment of particular endocrinological disorders—particularly in surgical operations. Unfortunately, the kinetics of hormonal secretion, metabolism, and clearance cannot be well understood with diagnostics that evaluate only a single form of the protein.

By way of example, approximately 100,000 patients undergo parathyroidectomy each year to treat primary hyperparathyroidism. Intraoperative measurement of intact parathyroid hormone ("IOPTH") is a critical step in the operative management of patients undergoing surgery for hyperparathyroidism because it is used to monitor the blood concentration of intact parathyroid hormone (PTH) and to confirm that the offending parathyroid gland has been removed. Measurement of Intraoperative PTH (IOPTH) reduces rates of full neck exploration as well as rates of re-operation to remove residual parathyroid tissue, resulting in decreased risk and morbidity to the patient. In many institutions, IOPTH measurements are routinely performed by sending patient specimens to a central lab which are then analyzed. Some institutions, such as The University of North Carolina at Chapel Hill (UNC), perform IOPTH measurements near or within the operating room (OR) suite, which has been shown to reduce specimen turnaround time and procedure costs. But, a low-cost and portable PTH assay could further reduce IOPTH costs and help broaden the adoption of performing IOPTH measurements within the OR suite.

The presently disclosed subject matter addresses the above-mentioned needs and other needs in the art.

SUMMARY

Disclosed in accordance with the presently disclosed subject matter is a method for determining concentrations of a target molecule and/or a variant thereof in a sample. In some embodiments, the method comprises: providing a sample comprising or suspected to comprise a target molecule and/or at least one variant thereof; exposing the sample to one or more recognition elements that bind to the target molecule and/or the at least one variant; detecting a signal associated with the binding of the target molecule to the one or more recognition elements and/or a signal associated with the binding of the at least one variant to the one or more recognition elements; and determining the concentration of the target molecule and/or the at least one variant thereof based on the signals.

Disclosed in some embodiments is a system for determining concentrations of a target molecule and at least one variant thereof in a sample. In some embodiments, the system comprises: a receiver adapted to receive a sample comprising or suspected to comprise a target molecule and the at least one variant thereof, the receiver comprising one or more recognition elements that bind to one or more epitopes in the target molecule and/or the at least one variant thereof.

In some embodiments, the target molecule and the at least one variant thereof comprise a protein and one or more fragment(s) thereof. In some embodiments, the target molecule and the at least one variant thereof comprise a hormone and/or one or more fragment(s) thereof. In some embodiments, the sample comprises a clinical fluid and/or a tissue aspirate.

In some embodiments, the one or more recognition elements are spatially distinguishable. In some embodiments, the one or more recognition elements are spectrally distinguishable. In some embodiments, the one or more recognition elements comprise an antibody, a peptide, an aptamer, and/or a combination thereof. In some embodiments, the one or more recognition elements bind one or more epitopes in the target molecule and/or the at least one variant thereof. In some embodiments, the one or more recognition elements bind to different epitopes of the target molecule and/or the at least one variant thereof.

In some embodiments, the one or more recognition elements have different sensitivities for the target molecule and the at least one variant thereof. In some embodiments, the one or more recognition elements have different sensitivities for a complex comprising a detectable moiety and the target and for a complex comprising a detectable moiety and the at least one variant thereof.

In some embodiments, the signal associated with the binding of the target molecule to the one or more recognition elements and/or the signal associated with the binding of the at least one variant thereof to the one or more recognition elements is/are compared to a known sensitivity of the one or more recognition elements for the target molecule and/or the at least one variant thereof to predict the concentration of the target molecule and/or the at least one variant thereof within the sample.

In some embodiments, the system comprises a detector for detecting a signal associated with the binding of the target molecule to the one or more recognition elements and/or a signal associated with the binding of the at least one variant to the one or more recognition elements. In some embodiments, the system comprises a processor for determining the concentration of the target molecule and/or the at least one variant thereof based on the signals. In some embodiments, the processor determines concentration by comparing the signal associated with the binding of the target molecule to the one or more recognition elements and/or the signal associated with the binding of the at least one variant thereof to the one or more recognition elements to a known sensitivity of the one or more recognition elements for the target molecule and/or the at least one variant thereof.

Accordingly, it is an object of the presently disclosed subject matter to provide methods and systems for determining concentrations of a target molecules and/or variant(s) thereof in a sample. This and other objects are achieved in whole or in part by the presently disclosed subject matter.

An object of the presently disclosed subject matter having been stated above, other objects and advantages of the presently disclosed subject matter will become apparent to those of ordinary skill in the art after a study of the following description of the presently disclosed subject matter and non-limiting Figures and Examples.

DETAILED DESCRIPTION

Figure 1:
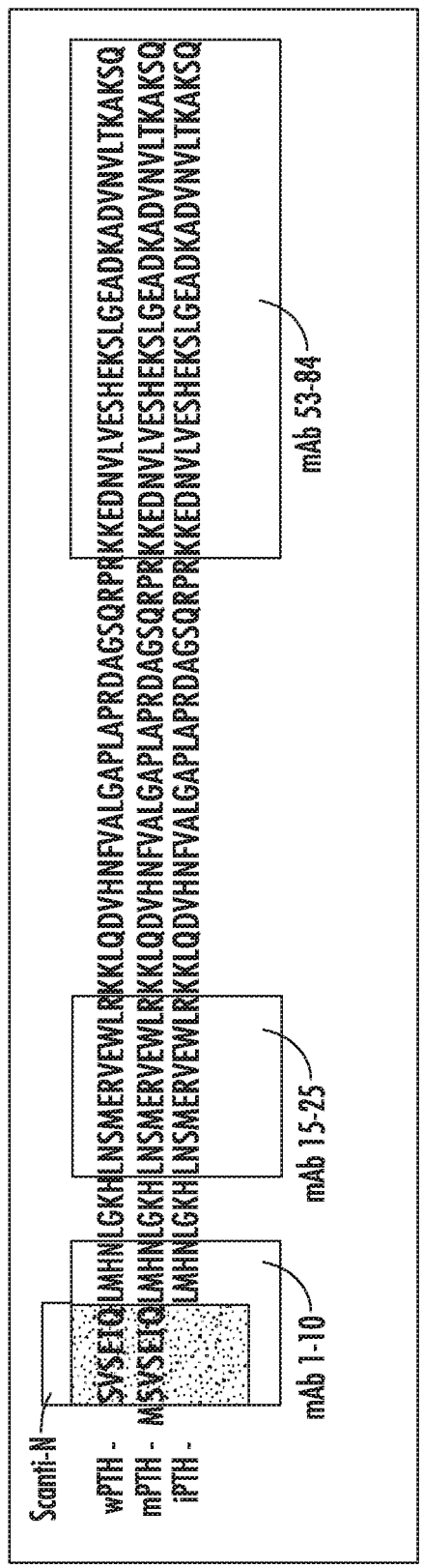
FIG. 1 is a schematic setting forth epitopes of PTH variants recognized by various antibodies. wPTH; SEQ ID NO: 1; iPTH; SEQ ID NO: 2; mPTH; SEQ ID NO: 6.

The presently disclosed subject matter will now be described more fully hereinafter with reference to the accompanying Figures and Examples, in which representative embodiments are shown. The presently disclosed subject matter can, however, be embodied in different forms and should not be construed as limited to the embodiments set forth herein. Rather, these embodiments are provided so that this disclosure will be thorough and complete, and will fully convey the scope of the embodiments to those skilled in the art. Certain components in the figures are not necessarily to scale, emphasis instead being placed upon illustrating the principles of the presently disclosed subject matter (in some cases schematically).

Unless otherwise defined, all technical and scientific terms used herein have the same meaning as commonly understood by one of ordinary skill in the art to which this presently described subject matter belongs. All publications, patent applications, patents, and other references mentioned herein are incorporated by reference in their entirety.

While the following terms are believed to be well understood by one of ordinary skill in the art, the following definitions are set forth to facilitate explanation of the presently claimed subject matter.

Following long-standing patent law convention, the terms "a", "an", and "the" refer to "one or more" when used herein, including in the claims.

As used herein, the term "about", when referring to a value or an amount, for example, relative to another measure, is meant to encompass variations of in some embodiments ±20%, in some embodiments ±10%, in some embodiments ±5%, in some embodiments ±1%, and in some embodiments ±0.1% from the specified value or amount, as such variations are appropriate. The term "about" can be applied to all values set forth herein.

As used herein, the term "and/or" when used in the context of a listing of entities, refers to the entities being present singly or in combination. Thus, for example, the phrase "A, B, C, and/or D" includes A, B, C, and D individually, but also includes any and all combinations and sub-combinations of A, B, C, and D.

The term "comprising", which is synonymous with "including," "containing," or "characterized by" is inclusive or open-ended and does not exclude additional, unrecited elements or method steps. "Comprising" is a term of art used in claim language which means that the named elements are present, but other elements can be added and still form a construct or method within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising", "consisting of", and "consisting essentially of", where one of these three terms is used herein, the presently disclosed and claimed subject matter can include the use of either of the other two terms.

As used herein, "significance" or "significant" relates to a statistical analysis of the probability that there is a non-random association between two or more entities. To determine whether or not a relationship is "significant" or has "significance", statistical manipulations of the data can be performed to calculate a probability, expressed in some embodiments as a "p-value". Those p-values that fall below a user-defined cutoff point are regarded as significant. In some embodiments, a p-value less than or equal to 0.05, in some embodiments less than 0.01, in some embodiments less than 0.005, and in some embodiments less than 0.001, are regarded as significant.

The presently disclosed subject matter can be used to detect target molecules and their variants. The term "variant" is used to include but is not limited to fragments, multimers, subunits and the like, of a given target molecule, including variants related to in vivo metabolic activity. In some embodiments, the target molecule and the at least one variant thereof comprise a protein and one or more fragment(s) thereof. In some embodiments, the target molecule and the at least one variant thereof comprise a hormone and one or more fragment(s) thereof.

The term "clinical fluid" or "clinical sample" is used to include materials derived from animals or humans including but not limited to whole blood, serum, plasma, urine, tissue aspirates, saliva, mucous, and any other samples derived from living tissues.

The presently disclosed subject matter relates in some embodiments to a multiplexed diagnostic system and method that are capable of determining the concentrations of target molecules and variants thereof, such as an original protein and its metabolic fragment(s). The multiplexing of the diagnostic can be performed, for example, spatially (such as via a microarray) or spectrally (such as via unique transduction elements; for background information on multiplexed assays using optical sensors, see reference (Ligler 2008).

Disclosed in accordance with the presently disclosed subject matter is a method for determining concentrations of a target molecule and/or a variant thereof in a sample. In some embodiments, the method comprises: providing a sample comprising or suspected to comprise a target molecule and/or at least one variant thereof; exposing the sample to one or more recognition elements that bind to the target molecule and/or the at least one variant; detecting a signal associated with the binding of the target molecule to the one or more recognition elements and/or a signal associated with the binding of the at least one variant to the one or more recognition elements; and determining the concentration of the target molecule and/or the at least one variant thereof based on the signals.

Disclosed in some embodiments is a system for determining concentrations of a target molecule and/or at least one variant thereof in a sample. In some embodiments, the system comprises: a receiver adapted to receive a sample comprising or suspected to comprise a target molecule and/or the at least one variant thereof, the receiver comprising one or more recognition elements that bind to one or more epitopes in the target molecule and/or the at least one variant thereof.

By the term "suspected to comprise" it is meant to refer to a sample that could comprise a target molecule and/or at least one variant thereof. To elaborate, the presently disclosed subject matter does not require the sample to have both a target and a variant. Methods and systems in accordance with the presently disclosed subject can thus pertain to situations where there could be a target and variant, but that also include cases where the sample is determined to not be a mixture. In fact, in case of original or initial uncertainty, the methods and systems of the presently disclosed subject matter can determine that only one of the molecules is present.

In some embodiments, the target molecule and the at least one variant thereof comprise a protein and/or one or more fragment(s) thereof. In some embodiments, the target molecule and the at least one variant thereof comprise a hormone and/or one or more fragment(s) thereof. In some embodiments, the sample comprises a clinical fluid and/or a tissue aspirate.

In some embodiments, the one or more recognition elements are spatially distinguishable. In some embodiments, the one or more recognition elements are spectrally distinguishable. In some embodiments, the one or more recognition elements bind one or more epitopes in the target molecule and/or the at least one variant thereof. In some embodiments, the one or more recognition elements bind to different epitopes of the target molecule and/or the at least one variant thereof.

In some embodiments, the one or more recognition elements have different sensitivities for the target molecule and the at least one variant thereof. In some embodiments, the one or more recognition elements have different sensitivities for complexes of tracer recognition molecules and the target and/or variant thereof. That is, in some embodiments, the one or more recognition elements have different sensitivities for a complex comprising a detectable moiety and the target and/or variant thereof. In some embodiments, the resulting signal from each of the one or more recognition elements is used to determine the concentration of the target molecule and/or the at least one variant thereof.

In some embodiments, two, three, four or more recognition elements can employed. By way of elaboration and not limitation, two or more recognition elements can be employed, wherein the two or more recognition elements distinguish the target molecule and the at least one variant thereof. Indeed, upon a review or the instant disclosure one of ordinary skill in the art would appreciate that any desired number of recognition elements can be employed, often depending on target molecule and variants thereof to be investigated.

In some embodiments, the signal associated with the binding of the target molecule to the one or more recognition elements and/or the signal associated with the binding of the at least one variant thereof to the one or more recognition elements is/are compared to a known sensitivity of the one or more recognition elements for the target molecule and/or the at least one variant thereof to predict the concentration of the target molecule and/or the at least one variant thereof within the sample. By way of elaboration and not limitation, in some embodiments, after exposing the sample to the recognition elements the signals associated with the binding of the target molecule and the at least one variant thereof to two or more distinguishing recognition elements are compared to the known sensitivities of each distinguishing recognition elements for the target molecule and the at least one variant thereof to predict concentrations of the target molecule and the at least one variant thereof within the sample.

Reference is now made to an example of an antibody microarray in accordance with the presently disclosed subject matter, which can discriminate between whole protein and a major fragment. This microarray can be constructed in a manner that allows clinical samples to be passed over it so that recognition elements bind to the target molecules. Different elements (spots) of the microarray can present unique recognition elements that bind to different epitopes of the original protein. By printing unique recognition elements with different sensitivities for the relevant forms of the target molecule(s) of interest in different spots, the resulting signal from each spot can be used to identify concentrations, such as the absolute or relative concentrations, of the intact protein and fragments of interest within the clinical sample.

In some embodiments, one can generate a diagnostic test to determine the concentration of the primary protein and one of the metabolic fragments. Metabolic fragments typically are generated by cleavage of the primary protein. Therefore, one spot (spot 1) can present a recognition element that recognizes an epitope that is present in the whole protein but that has been cleaved off in the metabolic fragment of interest. The other spot (spot 2) can present a recognition element that recognizes an epitope of the protein that also remains in the fragment. Spot 1 would only recognize the full protein, and spot 2 would recognize both the full protein and the fragment of interest. If the readout system requires a label, the detection recognition molecule of the sandwich can then be chosen to bind to an epitope that is on both the fragment of interest and the full protein. By knowing something about the relative sensitivities of spot 2 to the different molecules, the absolute concentrations of the two populations can be determined with the information from spot 1. This strategy can be implemented in more complicated situations to analyze more than one fragment derived from the protein.

The presently disclosed subject matter provides data comparable to that which is currently only obtained by using multiple tests or by using expensive, complex laboratory equipment like liquid chromatography and mass spectrometry. In some embodiments, the test disclosed herein is faster and less expensive, can be performed by minimally trained personnel, and can be performed using a small portable device. Therefore, this information can be obtained at new points in a clinical setting, and new criteria can be set that utilize this information.

The data from this new test can be compared to new criteria to increase the positive predictive value (PPV) and negative predictive value (NPV) of certain diagnostic tests. Representative tests (detailed examples below) include determining whether a parathyroidectomy needs to continue and determining whether a certain parathyroid gland is overacting or normal. A more accurate diagnostic directly decreases the incidence of resubmissions for surgery, and indirectly decreases the time and costs for current surgeries.

Thus, provided in some embodiments of the presently disclosed subject matter is a microfluidic point of care PTH device to detect PTH in the systemic blood from patients undergoing surgery for primary hyperparathyroidism. The microfluidic device can provide clinically relevant information from the PTH levels in parathyroid gland aspirate. Concentrations of whole PTH (amino acids 1-84) and intact PTH (amino acids 7-84) from clinical fluids can be accurately quantified using the novel microfluidic point of care device. The presently disclosed subject matter can thus meet a need for rapid and affordable IOPTH assays at least in part by developing a point-of-surgery PTH assay. In some embodiments, the system or analytical device is a portable device that is cost effective, provides rapid results, and is suitable for implementation in the surgical suite.

In accordance with some embodiments of the presently disclosed subject matter, a multiplexed diagnostic is provided using microarray technology. By using a microarray in the test cartridge or other receiver, more information can be generated from the test than from a single on-target capture element. In some embodiments the cartridges allow for on-chip replicates to be performed as well as providing internal standards to provide for background subtraction and normalization of the on-target capture spots to minimize inter-cartridge variability and enhance potential for quantitation. In addition, the microarray provides unique on-target capture spots that target different molecules or epitopes of the same molecule.

In some embodiments, capture or recognition elements are printed onto a single microarray-based test cartridge or other receiver. The responses of these cartridges can be tested against standards for a target molecule and one or more derivatives or variants thereof in buffered samples, such wPTH and iPTH standards, separately, to generate calibration curves. These curves are characterized to determine the standard error of calibration (SEC) and the standard error of prediction (SEP) for each target molecule and one or more variant(s) thereof. The target molecule and one or more variant(s) thereof can then be mixed and loaded onto the cartridge at varying ratios and the calibration curves can be used to predict the concentrations of target molecules within mixed samples. These predictions are compared to the absolute concentrations of the target molecule and one or more variant(s) thereof by calculating the SEP for each. Upon demonstration of the cartridges to predict a mixed sample of wPTH and iPTH, similar tests are performed in spiked clinical fluids (plasma, serum, and blood). As described herein, it is possible to use this information to generate an improved criterion with better negative predictive and positive predictive values. This can be tested with the aspirate from potential hyperfunctioning parathyroid glands and then later tested with the serum/plasma from a blood draw. The required quantitative dynamic range is likely to be different for these two types of tests, and it is possible that a given test is useful in one environment and not in the other. Receiving Operating Curves (ROC) can be generated and compared to those of the traditional diagnostic criterion that are used.

Figure 12:
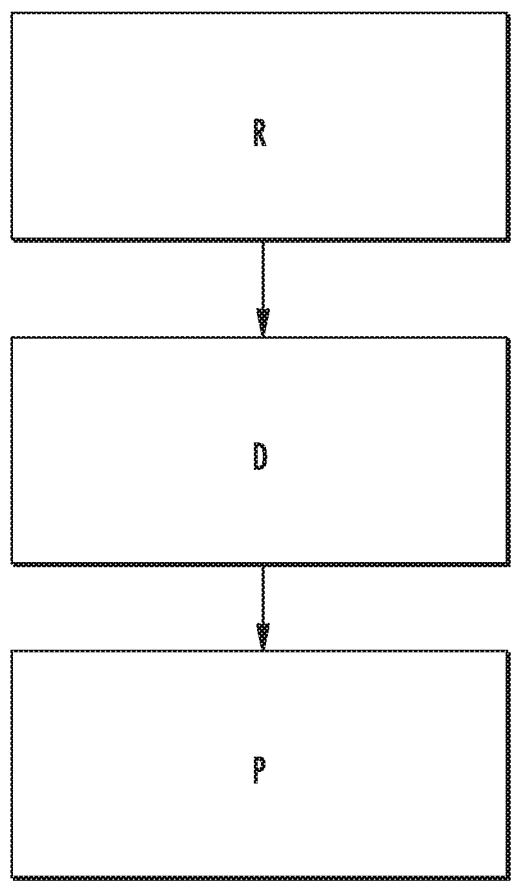
FIG. 12 is a schematic of a system in accordance with the presently disclosed subject matter.

Referring now to FIG. 12, disclosed in some embodiments is a system SYS for determining concentrations of a target molecule and/or at least one variant thereof in a sample. In some embodiments, system SYS comprises: a receiver R adapted to receive a sample comprising a target molecule and/or the at least one variant thereof, the receiver R comprising one or more recognition elements that bind to one or more epitopes in the target molecule and/or the at least one variant thereof. In some embodiments, system SYS comprises a detector D for detecting a signal associated with the binding of the target molecule to the one or more recognition elements and/or a signal associated with the binding of the at least one variant to the one or more recognition elements. In some embodiments, system SYS comprises a processor P for determining the concentration of the target molecule and/or the at least one variant thereof based on the signals. In some embodiments, detector D and processor P are embodied in a single component. In some embodiments, the processor determines concentration by comparing the signal associated with the binding of the target molecule to the one or more recognition elements and/or the signal associated with the binding of the at least one variant thereof to the one or more recognition elements to a known sensitivity of the one or more recognition elements for the target molecule and/or the at least one variant thereof.

In some embodiments, detector D and/or processor P employ a readout system developed by mBio Diagnostics (Boulder, Colo., United States of America), such as a portable fluorescence reader available under the trademark Snap-Esi™ (Ligler 2007, Lochhead 2011, Meneely 2012). Concentrations can be calculated using any suitable approach as would be understood by one of ordinary skill in the art upon a review of the instant disclosure. Representative approaches are disclosed in the examples, including but not limited to implementation of systems of differential equations. A variety of algorithms can be employed in lieu of or in addition to the differential equations used in the examples. In some embodiments, system SYS comprises portable and/or hand-held sensors or lateral flow tests.

Further, in some embodiments, the presently disclosed subject matter can be used to detect target molecules and their variants (such as fragments, multimers, subunits and the like) related to other disorders including other endocrinological disorders, such as but not limited to the following.

A. Exemplary Target Molecules and Variants Thereof (Including but not Limited to Fragments) for Multiplexing Technology in Addition to Parathyroid Hormone A useful diagnostic can include one or more of these molecules listed below and the related fragments. The number of amino acids (aa) is listed for many of these molecules. Any aa range (e.g. x-y aa) listed for a given variant indicates the range of aa of the original target molecule. Approximate concentrations are listed for some of the examples.

1. Amylin
Amylin (islet amyloid polypeptide (IAPP) (37 aa)
Proislet amyloid polypeptide—proIAPP (67 aa)
Non-fibril forming peptide (1-19 aa of human amylin, metabolic fragment)
Linked to Type 2 Diabetes—islet amyloid deposits
Unprocessed proIAPP is secreted in addition to amylin. This unprocessed proIAPP can serve as the granule upon which IAPP can accumulate and form amyloid. The repairing of the proIAPP processing may help prevent B-cell death and be a therapeutic approach for Type 2 diabetes. (~15 ng/L) normal
2. Angiotensinogen/Angiotensin
Angiotensinogen (453 aa)
Angiotensin 1 (10 aa, 25-143 pg/mL)), 2 (8 aa), 3 (7 aa), 4 (6 aa)
Causes vasoconstriction
Target for drugs that lower blood pressure.
3. Adrenocorticotropic hormone (ACTH)
Adrenocorticotropic hormone (1-39 aa)
Alpha-melanocyte stimulating hormone (1-13 aa)
Corticotropin-like intermediate peptide (CLIP) (19-39 aa)
Synthetic ACTH (1-24 aa)
   4. Atrial natriuretic peptide—regulated by degradation via neutral endopeptidase (NEP)
   5. Brain natriuretic peptide (BNP),
BNP (32 aa),
proBNP, (108 aa) cleaved to give BNP and NT-proBNP (76 aa)
Used for screening acute congestive heart failure
Secreted in response to excessive stretching of heart muscle cells
One of several molecules indicating traumatic brain injury
   6. Cholecystokinin—family of hormones, depending on aa length
Cholecystokinin—family of hormones, depending on aa length
Found in gastrointestinal system
   7. CRH (Corticotropin releasing hormone)
CRH (1-41 aa)
C-terminal fragment of CRH (9-41 aa) acts as CRH antagonist
Secreted in response to stress, Associated with Alzheimer's and major depression
Stimulates synthesis of ACT
   8. Cortistatin
Cortistatin 17 aa and Cortistatin 29 aa
Neuropeptide that depresses neuronal activity
   9. Erythropoetin 34 kDa, (10 mU/mL)
Erythropoetin 34 kDa, (10 mU/mL)
Doping w/recombinant/synthetic fragments
Controls red blood cell production
   10. Glucagon like peptide (7-37 aa) and (7-36 aa)
   11. Galanin, GMAP, GALP, Alarin
All are fragments of 123 aa protein pre-pro-galanin, encoded by GAL gene
Galanin
Galanin message-associated protein (GMAP)
Galanin-like peptide (GALP)
   12. Somatostatin—14 aa, 28 aa
   13. Prolactin
4 kDa, 16 kDa, 22 kDa, big (40-60 kDa), and big-big (>100 kDa)
   14. Pro-opiomelanocortin (POMC)-related end-products
Gamma-Melanotropin (gamma-MSH)
Adrenocorticotropic hormone (ACTH) (AKA Corticotropin)
Alpha-Melanotropin (alpha-MSH)
Corticotropin-like Intermediate Peptide (CLIP)
Beta-Melanotropin (beta-MSH)
Beta-Lipotropin (beta-LPH)
Gamma-Lipotropin (Gamma-LPH)
Beta-Endorphin
   15. Orexin A (33 aa)
Orexin B (28 aa)
   16. Instead of or in addition to fragments, look at multimers of a single protein.
Adiponectin—244 aa, (~5 ug/mL)
High molecular weight forms
Quantify concentration of monomer, trimer, hexamer, and dodecamer
Ratios can indicate risk factor of diabetes, coronary artery disease, metabolic syndromes
   17. Instead of fragments or multimers, look at proteins that are composed of multiple subunits that share 1 or more subunits and are different in 1 or more subunits.
Luteinizing Hormone (LH), Folicle Stimulating Hormone (FSH), Thyroid-Stimulating Hormone (TSH), and Human Chorionic Gonadotropin (HCG) all have the same alpha subunit but have different beta subunits B. Additional Alternatives In some embodiments, the presently disclosed methods and systems employ a technique in which the detection is spectrally multiplexed instead of and/or in addition to spatially multiplexed. That is, in some embodiments, the one or more recognition elements are spectrally distinguishable.

In some embodiments, the presently disclosed methods and systems employ aptamers or peptides, such as combinatorially selected aptamers or peptides, in place of antibodies as the bio-recognition molecules. That is, in some embodiments, the one or more recognition elements comprise an antibody, a peptide, an aptamer, and/or a combination thereof.

A variety of algorithms can replace the differential equations used to describe the system in the examples.

In some embodiments, the presently disclosed methods and systems incorporate multi-target assays for intact and modified proteins into a variety of portable and hand-held sensors or lateral flow tests.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The possible targets are not limited to PTH and its variants.

Example 1

PTH Testing for Initial Patient Screening and Intraoperative PTH Testing

One example where the presently disclosed subject matter can be employed is in the IOPTH measurements during a parathyroidectomy. Physiologically, PTH is originally synthesized as a 115 amino acid polypeptide called pre-pro-PTH. This peptide is cleaved at the N-terminus within parathyroid cells to pro-PTH and then to PTH (84 amino acids). This whole PTH (amino acids 1-84) (wPTH; SEQ ID NO: 1) is stored in the parathyroid glands and is secreted into the blood where it increases the rate of bone resorption. It is cleared by the liver and kidneys as well as broken down into smaller polypeptides (via peripheral metabolism) like intact PTH (amino acids 7-84) (iPTH; SEQ ID NO: 2) (Potts 2013). These C-terminal fragments are cleared through similar processes (by the liver and kidneys and the peripheral metabolism into shorter fragments), but the rates of iPTH clearance can be different than that of wPTH. In fact, these large C-terminal fragments of PTH have been observed to have a longer circulation half-life (~20 min) than wPTH (~2 min) (Yamashita 2003).

The primary function of wPTH is to stimulate the release of calcium from the bones into the blood. In healthy individuals, wPTH is released in response to low calcium concentrations in order to return to the desired calcium homeostasis. Normal concentrations of ionized calcium in the serum are 1.19-1.34 mM, and normal concentrations of PTH are 1.0-6.8 pM. However, there are instances where this feedback mechanism does not function properly, and these concentrations are either too high or too low. Because calcium concentrations need to be tightly regulated within normal levels for an individual to lead a full, healthy life, interventions are necessary (Potts 2013).

Primary hyperparathyroidism is a disorder where the systemic PTH concentrations are abnormally elevated as a result from the hyper-secretion of PTH by one or more parathyroid glands. This hyper-secretion is typically due to an adenoma in the gland. Approximately 80-85% of these cases display a single hyper-functioning gland and 15-20% of these cases display multiple. There are approximately 100,000 new cases of primary hyperparathyroidism appearing in the United States each year (Udelsman 2002, Pelleiteri 2013, Grant 2005). The elevated systemic PTH levels stimulate bone resorption which causes damage to the bone and deleterious, elevated calcium concentrations in the blood. The standard of care is to remove the hyper-secreting parathyroid gland as identified, if possible, with medical imaging and then determine whether additional glands need to be removed during the surgical procedure. After some time, the systemic PTH is expected to drop to normal levels following the removal of all over-acting glands, and, fortunately, wPTH has a very short circulating half-life (Inabnet 2004).

There has been significant debate in the field regarding the characteristic change in PTH that best indicates a successful surgery. The Miami criterion is the most well-known standard upon which surgeons use the results from intraoperative PTH assays. It states that the surgery is complete/successful (meaning no additional glands should be removed) if the systemic level of PTH drops to less than 50% of the original levels after 10 minutes (Irvin 1991, Irvin 1993, Greene 2009).

Many different variations of the PTH assay have been developed over the years (Meyer 2009). The most common type of assay that is currently being used is termed the $2^{nd}$ generation PTH assay (Goodman 2005). These assays have been shown to recognize both wPTH and iPTH, and these assays output a single PTH measurement. One group recently proposed using a kinetics-based approach with a $2^{nd}$ generation assay. They fit the IOPTH data with a single secretion and a single consumption term, and reported how the secretion rate changed upon excision (Bieglmayer 2002). While they reported an improvement on identifying successful surgeries, other groups have since reported that their criterion is no better than the Miami Criterion. This could be because the complex interplay between wPTH and iPTH could not be accounted for by fitting a simplified kinetic model with data from a $2^{nd}$ generation assay (Carneiro 2003). At the time, the cause of this problem was poorly understood (Gao, 2005).

A newer generation of the PTH-assay only recognizes wPTH by using an antibody in the sandwich immunoassay that recognizes the first several amino acids of the N-terminus. These assays are sometimes referred to as $3^{rd}$ generation PTH assays. Some groups have compared these $3^{rd}$ generation assays with the $2^{nd}$ generation assays to determine whether new criteria can be set (Caron 2009, Cavalier 2014). However, while the ratio of $3^{rd}$ generation response to $2^{nd}$ generation response has found some utility, the limited use of the two separate assays has not generated a new criterion for a successful parathyroidectomy to date (Boudou 2005).

The presently disclosed subject matter provides for the elucidation of the absolute or relative concentrations of wPTH and iPTH. For a parathyroidectomy, this could be performed at different time points after the removal of the over-acting gland to obtain time-dependent concentrations of these different protein subpopulations.

Quantitation of wPTH and iPTH in a Mixed Sample on Separate Cartridges (CL1).

Cartridges were developed using a readout system developed by mBio Diagnostics (Boulder, Colo., United States of America) that employed a microarray to be used with one of their portable fluorescence readers (available under the trademark Snap-Esi™) (Ligler 2007, Lochhead 2011, Meneely 2012). In a representative, non-limiting microarray embodiment using a single capture antibody, two different fluorescence detection antibodies were used in adjacent cartridges. These unique detection antibodies had different relative sensitivities to wPTH and iPTH, allowing the responses of the adjacent cartridges to offer information to determine the concentrations of wPTH and iPTH in a mixed sample.

The hormone (wPTH) and the targeted variant (iPTH) for this example are further described below.

```
Whole PTH (1-84 aa, wPTH; SEQ ID NO: 1)
Molecular Weight (MW): 9.4 kDa

Isoelectric Point (pI): 9.10

AA Sequence:
SVSEIQLMHN LGKHLNSMER VEWLRKKLQD VHNFVALGAP

LAPRDAGSQR PRKKEDNVLV ESHEKSLGEA DKADVNVLTK AKSQ

Intact PTH (7-84 aa, iPTH; SEQ ID NO: 2)
MW: 8.8 kDa pI: 9.46

AA Sequence:
LMHN LGKHLNSMER VEWLRKKLQD VHNFVALGAP LAPRDAGSQR

PRKKEDNVLV ESHEKSLGEA DKADVNVLTK AKSQ
```

The antibodies used for this example are further described below. Scanti-N and mAb 15-25 were both fluorescently labeled with Alexa Fluor 647 and served as the detection antibodies. The mAb 53-84 antibody served as the capture antibody in the diagnostic. FIG. 1 shows a representation of the approximate epitopes that are recognized by the various antibodies used in this example. Note that mAb 1-10 and mPTH are not used in Example 1.

Scanti-N (binds epitope SVSEIQ, SEQ ID NO: 3; see also FIG. 1): Anti-Human PTH, Scantibodies, Santee, Calif., United States of America, polyclonal goat antibody (IgG), 3AG668.

mAb 15-25 (binds epitope LNSMERVEWLR, SEQ ID NO: 4; see also FIG. 1): Anti-Human PTH, Abcam, Cambridge, Mass., United States of America, monoclonal mouse antibody (IgG), ab14493.

mAb 53-84 (binds epitope KKEDNVLVESHEK-SLGEADKADVNVLTKAKSQ, SEQ ID NO:5; see also FIG. 1): Anti-Human PTH, US Bio, Salem, Mass., United States of America, monoclonal mouse antibody (IgG), P3108-91B.

Figure 2:
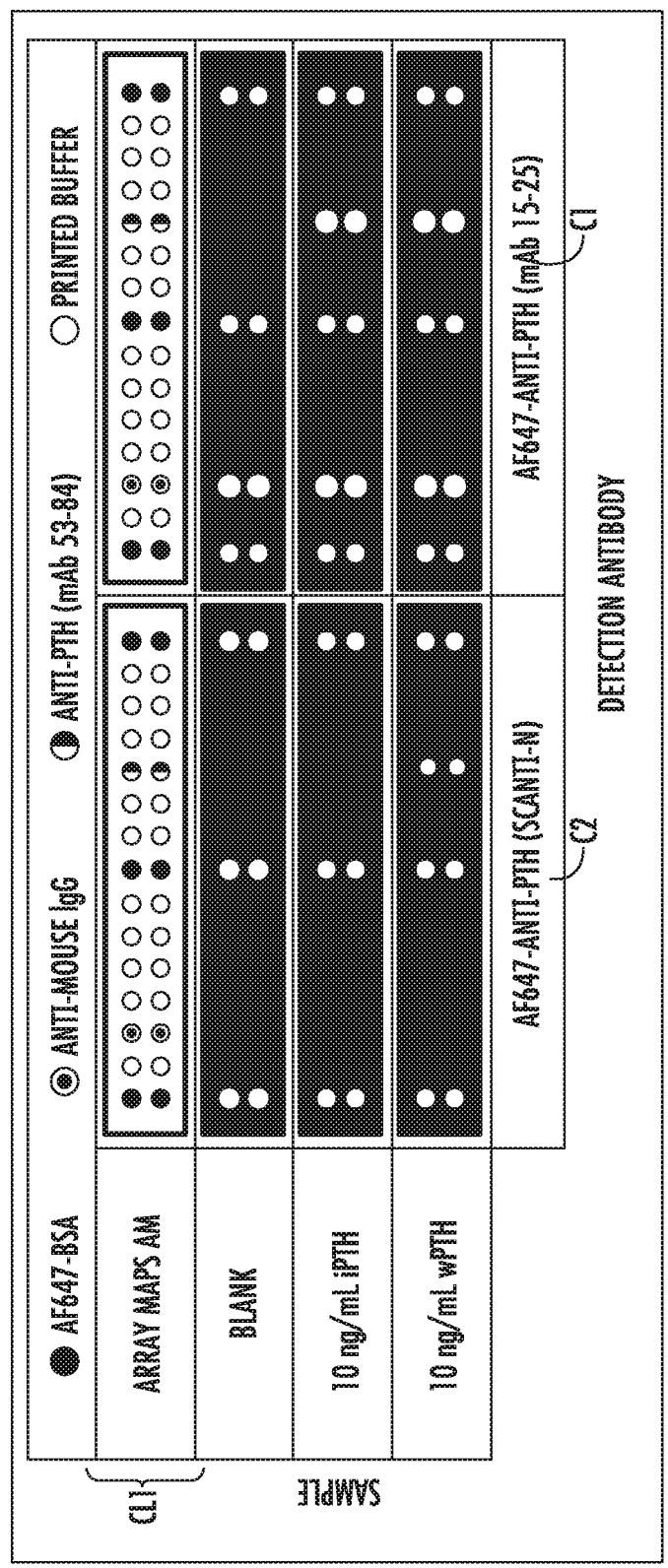
FIG. 2 is an example cartridge layout (cartridge layout #1, CL1) with mAb 53-84 capture spots for the cartridge employed to obtain the digital images also shown in FIG. 2 with samples of wPTH and iPTH with two different detection antibodies (mAb 15-25 and Scanti-N)

A microarray MA was printed in a microfluidic cartridge as described in FIG. 2, in a configuration CL1 with mAb 53-84. FIG. 2 provides the orientation of the images along with the images seen on the screen during the imaging process. In this case, the sample is loaded at an inlet on the right, and the sample flows from right to left. As shown by array maps AM, microarray MA is composed of 2 rows and 15 columns each. The mAb 53-84 capture antibody was printed in spots row 1, column 11 (numbering from left to right) and row 2, column 11 (numbering from left to right), as indicated with a vertical half solid circle, vertical half open circle symbol in FIG. 2. The AF647-BSA spots at row 1, columns 1, 8, 15 (numbering from left to right) and row 2, columns 1, 8, 15 (numbering from left to right), are printed bovine serum albumin that had been labeled with Alexa Fluor 647, as indicated by solid circles. These spots should fluoresce when the cartridge is excited and are used to indicate the location of the microarray MA and normalize the on-target signal. The spots at row 1, columns 2, 4, 7, 8, 10 (numbering from left to right) and row 2, columns 2, 4, 7, 8, 10 (numbering from left to right), as identified as open circles, indicate spots where only buffer was printed. These spots enabled background subtraction of the neighboring spots. The Anti-Mouse IgG spots at row 1, column 3 and row 2, column 3, as indicated by an open circle with a concentric solid circle, capture fluorescent detection antibody (if the detection antibody is mouse IgG) that makes it to the end of the channel. Light is applied at a lens end of the cartridge.

Figure 3:
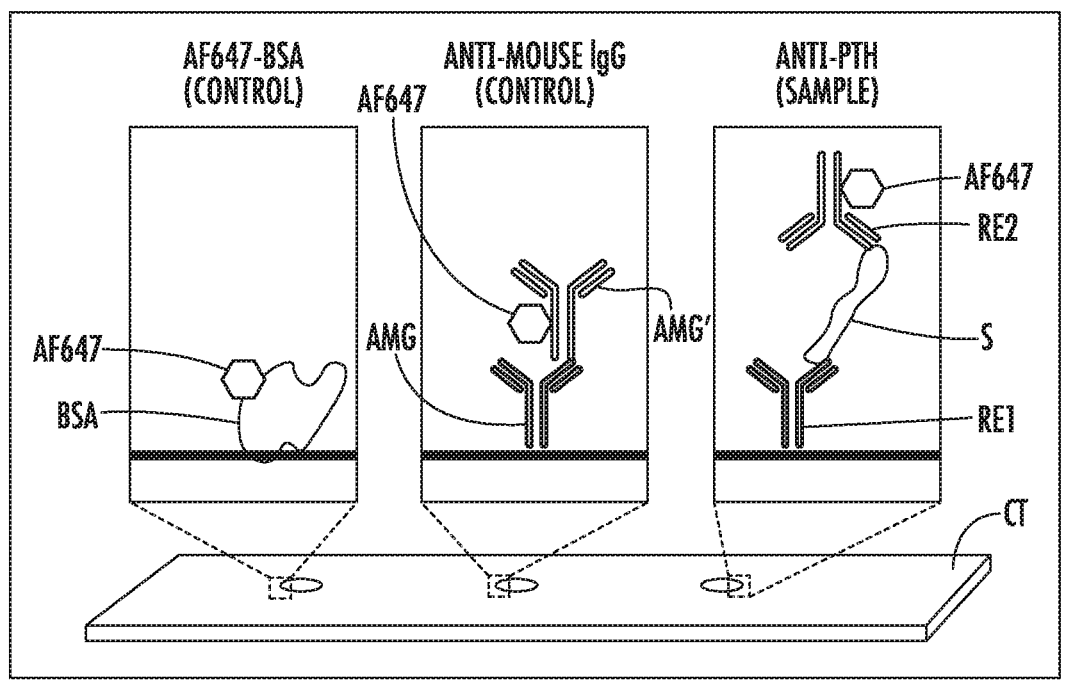
FIG. 3 is a schematic of various printed microarray spots in cartridges.

FIG. 3 is a schematic of a cartridge CT showing how the various spots function when exposed to various samples. Hexagons AF647 are indicative of the Alexa Fluor 647 fluorophore, which is a representative detectable moiety in accordance with the presently disclosed subject matter, that present as bright spots if present. BSA spots, labeled with AF647, act as a control and will always fluoresce if the system is on. Anti-mouse IgG (AMG) spots also act as a control and will fluoresce if fluorescently-labeled mouse IgG AMG' is present in the sample. The Anti-PTH recognition element RE1 spots (e.g., P3108-91B) should fluoresce if the targeted sample S is present and bound by a labeled recognition element RE2, such as AF647 labeled mAb 15-25 and or AF647 labeled Scanti-N. Note that AMG' and the RE2 would be the same molecule if RE2 were a mouse IgG.

In this example, the cartridge presents one type of on-target capture antibody (mAb 53-84). To determine the absolute concentrations of a mixed sample of wPTH and iPTH using this format, each sample was run on two cartridges where each cartridge used a unique type of detection antibody (Cartridge 1 C1 used AF647 labeled mAb 15-25 and Cartridge 2 C2 used AF647 labeled Scanti-N).

For each sample, the following method was used:
1. Prepare desired mixture of wPTH and iPTH.
2. Mix 25 microliters (µL) of sample with 11 µL 83.33 nM AF647-mAb 15-25 to make Solution 1 and in another solution mix 25 µL of sample with 11 µL 83.33 nM AF647-Scanti-N to make Solution 2.
3. After 30 seconds of mixing, load Solution 1 onto Cartridge 1 and Solution 2 onto Cartridge 2 and leave flat.
4. After 20 minutes, add 100 µL wash buffer to each cartridge.
5. After 1.75 min, scan each cartridge using Snap-Esi™ Reader The images collected for each of three different samples are shown in FIG. 2: Lower set of panels—Sample 1: 10 ng/mL wPTH, 0 ng/mL iPTH; Middle set of panels—Sample 2: 0 ng/mL wPTH, 10 ng/mL iPTH; Upper set of panels—Sample 3: 0 ng/mL wPTH, 0 ng/mL iPTH). In FIG. 2, example scans of cartridge definition CL1 with samples of wPTH and iPTH with two different detection antibodies (mAb 15-25—Cartridge 1, C1 and Scanti-N—Cartridge 2, C2) are shown. Note that the anti-mouse IgG spots do not recognize the Scanti-N detection antibody because it is a goat IgG.

For each image, the following method was used to obtain an averaged, normalized, and background subtracted value to be reported.
1. Calculate the intensity of each predefined spot of the image.
2. Intensity of adjacent buffer spots subtracted from on-target (P3108-91B) and AF647-BSA spots
3. Subtracted on-target intensity is normalized by dividing by intensity of subtracted control AF647-BSA printed spots
4. The duplicate normalized, subtracted on-target spots are averaged to give the final reported value (F1 for Cartridge 1 and F2 for Cartridge 2).

Figure 4:
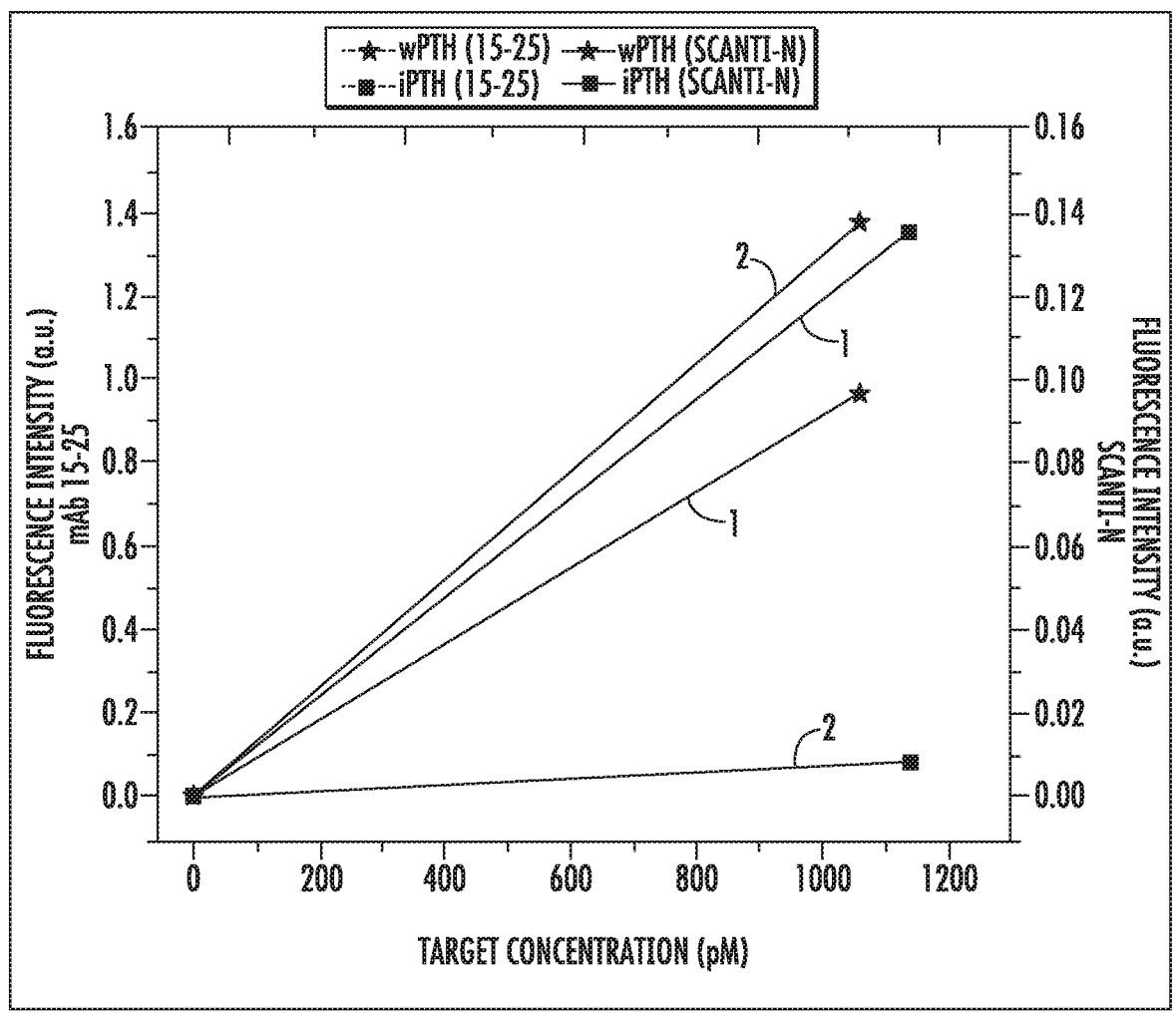
FIG. 4 is a plot showing responses of mAb 53-84 spots to concentrations of wPTH (stars) and iPTH (squares) for different detection antibodies (1: Cartridge 1 w/ mAb 15-25, 2: Cartridge 2 w/ Scanti-N).

The final reported value for Cartridge 1 and 2 for each sample was then plotted against the actual concentration of each target to obtain the various calibration curves. This is shown in FIG. 4, which displays the response of each target on both cartridges using the associated detection antibodies. The data labelled with 1 was obtained using Cartridge 1 with mAb 15-25, and the data labelled with 2 was obtained using Cartridge 2 with Scanti-N. Note that Cartridge 1—using mAb 15-25 as the detection antibody—has a similar sensitivity to wPTH and iPTH, while Cartridge 2—using Scanti-N—responds to wPTH at a much greater sensitivity in comparison to iPTH. This arises due to the fact that the Scanti-N antibody is specific for the N-terminus of the wPTH, and this epitope is not present in the iPTH. In FIG. 4, responses of mAb 53-84 spots to concentrations of wPTH (stars) and iPTH (squares) for different detection antibodies (1: Cartridge 1 w/ mAb 15-25, 2: Cartridge 2 w/ Scanti-N).

Surface-based assays typically have a linear region where the signal correlates to the target concentration. Using the multiple cartridges with the appropriate, unique detection antibodies as described in this example, a system of linear equations can be generated to correlate the fluorescence intensities from the different cartridges to the absolute concentrations within the mixture. The system can be described using Equation 1. In this equation, F1 is indicative of the final reported value for Cartridge 1 and F2 is the final reported value for Cartridge 2. The slopes and intercepts can be obtained through the data in FIG. 4.

$$\begin{bmatrix} F_1 \\ F_2 \end{bmatrix} = \begin{bmatrix} m_{1w} & m_{1i} \\ m_{2w} & m_{2i} \end{bmatrix} \cdot \begin{bmatrix} [wPTH] \\ [iPTH] \end{bmatrix} + \begin{bmatrix} b_1 \\ b_2 \end{bmatrix} \quad \text{Equation 1}$$

Once the slopes and intercepts for the system of equations have identified via calibration, this multi-cartridge approach can be used to predict the, concentrations of a mixed sample using Equation 2. Note that the $m_{1w}:m_{1i}$ ratio must be significantly different than $m_{2w}:m_{2i}$ ratio to enable the accurate prediction of a mixed sample $$\begin{bmatrix} [wPTH] \\ [iPTH] \end{bmatrix} = \begin{bmatrix} m_{1w} & m_{1i} \\ m_{2w} & m_{2i} \end{bmatrix} \setminus \left( \begin{bmatrix} F_1 \\ F_2 \end{bmatrix} - \begin{bmatrix} b_1 \\ b_2 \end{bmatrix} \right) \quad \text{Equation 2}$$

Figure 5:
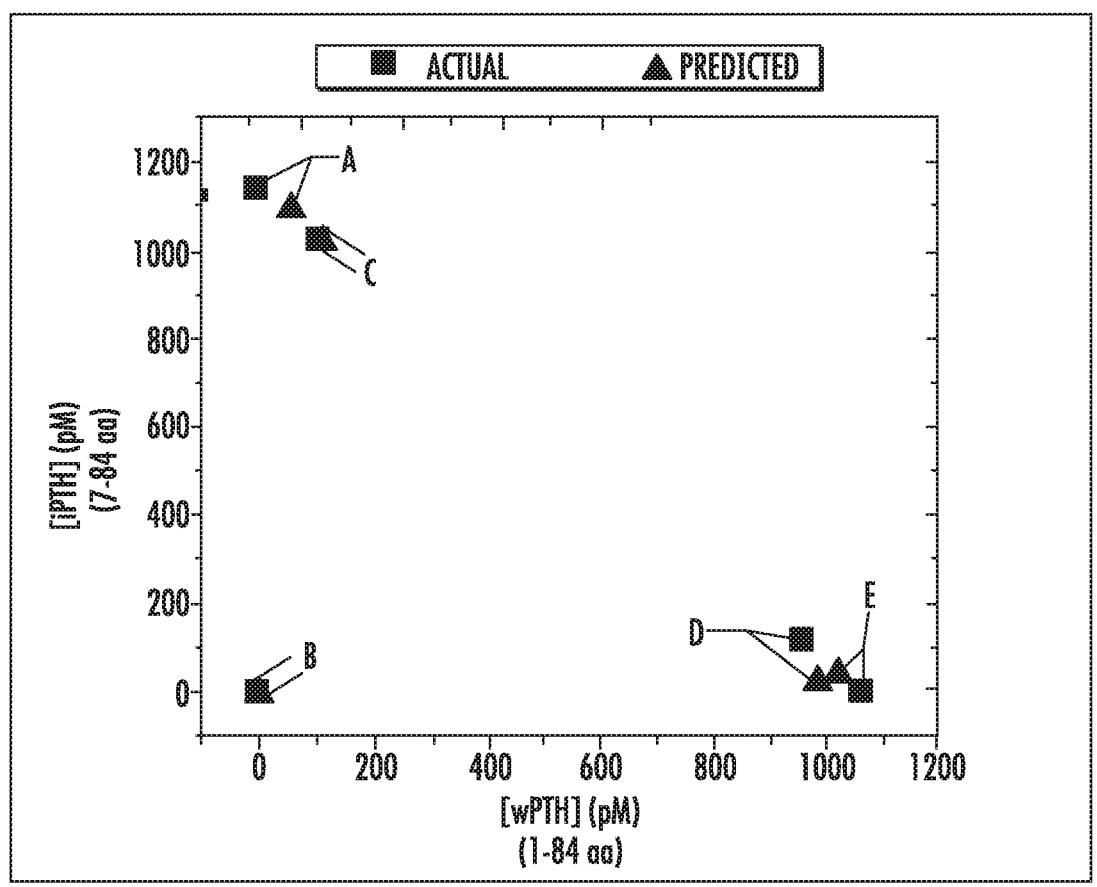
FIG. 5 is a plot showing actual concentrations (squares) and predicted concentrations (triangles) of wPTH and iPTH in various mixed samples.

FIG. 5 is an example of the utility of the multi-cartridge approach. Multiple samples were tested using the aforementioned method, and the concentrations of wPTH and iPTH were predicted using the final, reported fluorescence intensities from each cartridge and the associated system of equations. The accuracy of the prediction is indicated by the distance between the triangle and the square for a given set of markers, where shorter distances equate better accuracies. In FIG. 5, shown are actual concentrations (squares) and predicted concentrations (triangles) of wPTH and iPTH in various mixed samples. The same letter represents the pair of actual and predicted data. A indicates a sample with 0 ng/mL wPTH and 10 ng/mL iPTH. B indicates a sample with 0 ng/mL wPTH and 0 ng/mL iPTH. C indicates a sample with 1 ng/mL wPTH and 9 ng/mL iPTH. D indicates a sample with 9 ng/mL wPTH and 1 ng/mL iPTH. E indicates a sample with 10 ng/mL wPTH and 1 ng/mL iPTH.

The orientation of these assays could be flipped to where the mAb 15-25 and Scanti-N serve as the capture antibodies on a single cartridge and mAb 53-84 serve as the fluorescently labeled detection antibody. Further, more cartridge/ detection antibody combinations could optionally be run in parallel. And, if done, Equations 1 and 2 could be made more complex and could still be used predict the concentrations of wPTH and iPTH and/or for any other desired purpose.

Example 2

Quantitation of Whole PTH and Methionine-Whole PTH on a Single Multiplexed Cartridge In this example, an approach to quantify the concentrations of a protein and a methionine version of the protein using a single multiplexed cartridge is presented. Recombinant proteins are often used in place of the natural proteins for various purposes. It could be essential for the recombinant protein to be identical in amino acid sequence to the native protein. However, depending on the post-translation processes by the supplier, it is possible that the recombinant protein differs from the natural protein in that it retains an additional methionine residue at the N-terminus. Methionine is often a part of the pro-protein, as it is coded for by the most common start codons, but it is typically cleaved by proteases in nature. Some suppliers do not remove the methionine residue added to the sequence during the production process.

This example shows that it is possible to quantify the concentration of a mixture of two proteins that differ by only one amino acid using the single multiplexed cartridge. This example describes representative bio-recognition elements that have been identified, screened, and shown to work in approaches similar to those described in Example 1.

The capability to measure a protein with an additional methionine or other variations of recombinant proteins can be of use in the development, processing, or use of proteins for therapeutics, diagnostics, food, or other purposes.

Cartridges were developed using a readout system developed by mBio Diagnostics (Boulder, Colo., United States of America) that employed a microarray to be used with one of their portable fluorescence readers (available under the trademark Snap-Esi™). In a representative, non-limiting microarray embodiment, two-unique capture elements have different relative sensitivities to wPTH and mPTH, and the information from the microarray can be used to determine the concentrations of wPTH and mPTH in a mixed sample.

The hormone (wPTH) and the targeted variant (mPTH) for this example are further described below.

Whole PTH (1-84 aa, wPTH; SEQ ID NO: 1)
MW: 9.4 kDa pI: 9.10

AA Sequence:
SVSEIQLMHN LGKHLNSMER VEWLRKKLQD VHNFVALGAP

LAPRDAGSQR PRKKEDNVLV ESHEKSLGEA DKADVNVLTK AKSQ

Methionine-whole PTH (m + 1-84 aa, nnPTH;
SEQ ID NO: 6)

MW 9.6 kDa pI: 9.10

AA Sequence:
MSVSEIQLMHN LGKHLNSMER VEWLRKKLQD VHNFVALGAP

LAPRDAGSQR PRKKEDNVLV ESHEKSLGEA DKADVNVLTK AKSQ

The antibodies used for this example are further described below. The mAb 1-10 and mAb 15-25 were printed in unique spots and served as two different capture antibodies in a single diagnostic cartridge. The mAb 53-84 antibody was fluorescently labeled with Alexa Fluor 647 and served as the detection antibody. FIG. 1 shows a representation of the approximate epitopes that are recognized by the various antibodies used in this example. Note that Scanti-N and iPTH are not used in Example 2.

mAb 1-10 (binds epitope SVSEIQLMHN, SEQ ID NO: 7; see also FIG. 1): Anti-Human PTH, US Bio, monoclonal mouse antibody (IgG), P3108-87A.

mAb 15-25 (binds epitope LNSMERVEWLR, SEQ ID NO: 4; see also FIG. 1): Anti Human PTH, Abcam, monoclonal mouse antibody (IgG), ab14493.

mAb 53-84 (binds epitope KKEDNVLVESHEK-SLGEADKADVNVLTKAKSQ, SEQ ID NO:5; see also FIG. 1): Anti-Human PTH, US Bio, monoclonal mouse antibody (IgG), P3108-91B.

Figure 6:
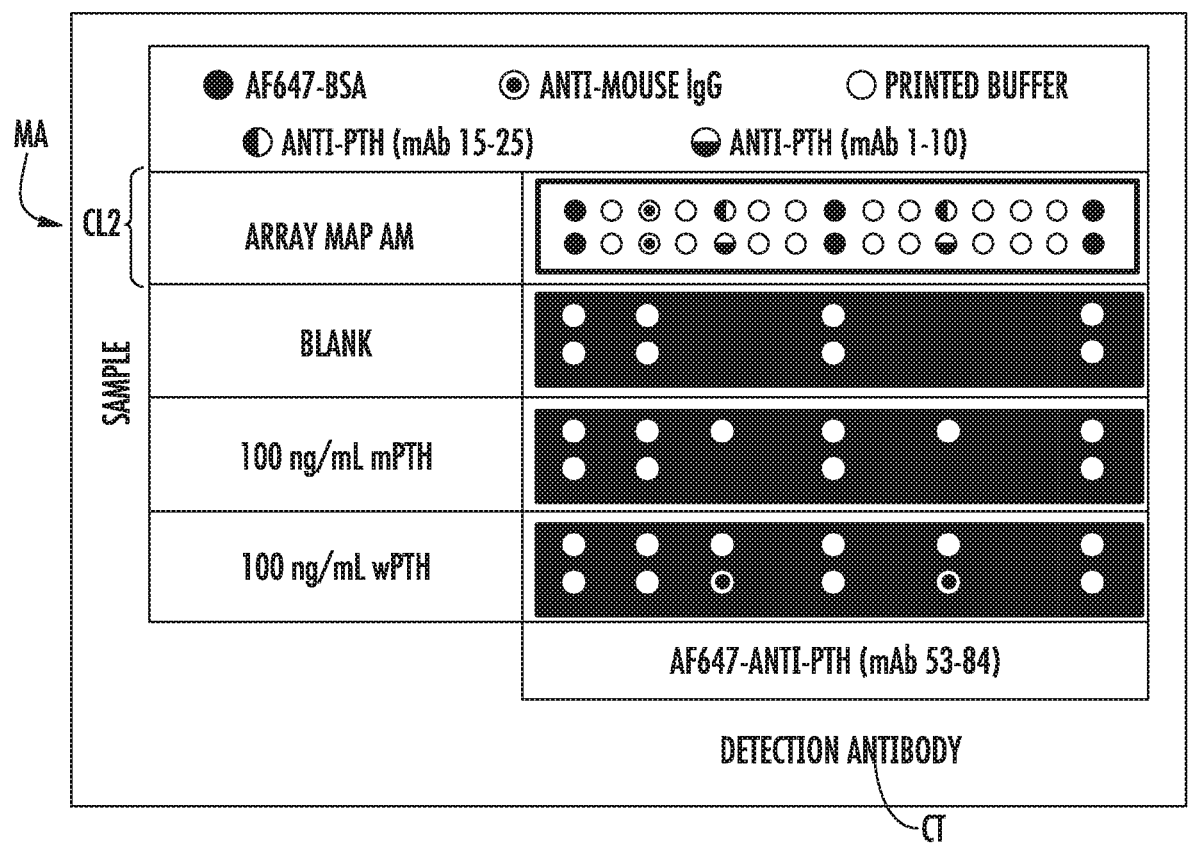
FIG. 6 is a schematic showing an example multiplexed cartridge layout (cartridge layout #2, CL2) with mAb 15-25 (ab14493) and mAb 1-10 (P3108-87A) printed spots used to obtain the series of digital images shown in FIG. 6 of example scans with wPTH and mPTH.

A microarray MA was printed in a microfluidic cartridge CT as described in FIG. 6. FIG. 6 provides the orientation CL2 of the images along with the images seen on the screen during the imaging process. In this case, the sample is loaded at an inlet on the right, and the sample flows from right to left. As shown by array map AM, microarray MA is composed of 2 rows of 15 columns each. The mAb 1-10 capture antibody was printed in spots at row 2, column 5 and row 2, column 11 (numbering from left to right), as indicated with a symbol having a horizontal half open circle and a horizontal half solid circle and the mAb 15-25 capture antibody was printed in spots at row 1, column 5 and row 1, column 11 (numbering from left to right), as indicated with a symbol having a vertical half open circle and a vertical half solid circle. The AF647-BSA spots at row 1, columns 1, 8 and 15 and row 2, columns 1, 8 and 15 (numbering from left to right) are printed bovine serum albumin that had been labeled with Alexa Fluor 647, as indicated by solid circles. These spots should fluoresce when the cartridge is excited and are used to indicate the location of the microarray MA and normalize the on-target signal. The spots at row 1, columns 2, 4, 6, 7, 9, 10, and 12-14 (numbering from left to right) and row 2 columns 2, 4, 6, 7, 9, 10, and 12-14 (numbering from left to right) identified as open circles, indicate spots where only buffer was printed. These spots enabled background subtraction of the neighboring spots. The Anti-Mouse IgG spots at row 1, column 3 and row 2, column 3 (numbering from left to right) as indicated by an open circle with a concentric solid circle capture fluorescent detection antibody (if the detection antibody is mouse IgG) that makes it to the end of the channel. Light is applied at a lens at the end of the cartridge.

In this example, the cartridge CT presents two types of on-target capture antibody (mAb 1-10 and mAb 15-25). Using this format, it is possible to determine the absolute concentrations of a mixed sample of wPTH and mPTH on a single cartridge with a single detection antibody (AF647-labeled mAb 53-84).

For each sample, the following method was used:
1. Prepare desired mixture of wPTH and mPTH.
2. Add 32 μL of target sample in buffer
3. After 60 minutes, load 80 μL of 25 nM AF647-mAb 53-84 and place on incline
4. After 2 minutes on incline, move to flat surface.
5. After 8 minutes, add 100 μL wash buffer and place on incline
6. After 2 minutes, scan cartridge using Snap-Esi™ Reader.

The images collected for each of three different samples (Sample 1, lower panel: 100 ng/mL wPTH, 0 ng/mL mPTH; Sample 2, middle panel: 0 ng/mL wPTH, 100 ng/mL mPTH; Sample 3, upper panel: 0 ng/mL wPTH, 0 ng/mL mPTH—BLANK) are shown in FIG. 6, which shows example scans of cartridge definition CL2 with wPTH and mPTH.

For each image, the following method was used to obtain an averaged, normalized, and background subtracted value to be reported.
1. Calculate the intensity of each predefined spot of the image.
2. Intensity of adjacent buffer spots subtracted from the different on-target spots (ab14493 and P3108-97A) and BSA-AF647 spots.
3. Subtracted on-target intensity is normalized by dividing by intensity of subtracted control BSA-AF647 printed spots.
4. The duplicate normalized, subtracted on-target spots are averaged to give the final reported value (F1 for top (mAb 15-25) and F2 for bottom (mAb 1-10)).

Figure 7:
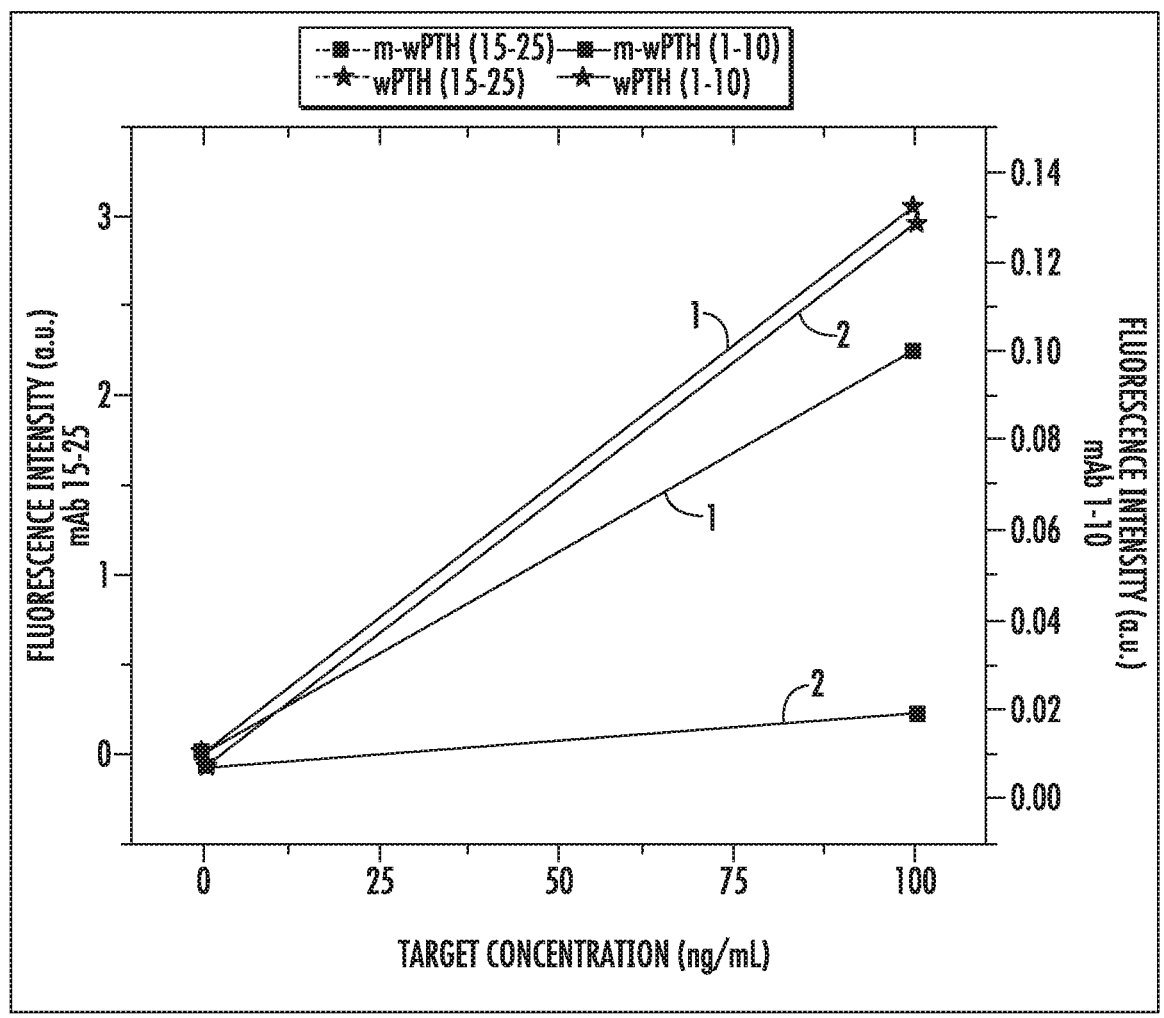
FIG. 7 is a plot of responses of mAb 15-25 and mAb 1-10 spots to concentrations of mPTH (squares) and wPTH (stars).

The final reported value for capture spot 1 and 2 (F1 and F2) for each sample was then plotted against the actual concentration of each target to obtain the various calibration curves. This is shown in FIG. 7, which displays the response of each target on both capture antibodies of the cartridge. The data labelled with 1 was obtained using the mAb 15-25 capture spot, and the data labelled with 2 was obtained using the mAb 1-10 capture spot. Note that the spot with mAb 15-25 as the capture antibody has a similar sensitivity to wPTH (stars) and mPTH (squares), while the spot with mAb 1-10 as the capture antibody responds to wPTH at a much greater sensitivity in comparison to mPTH. This arises due to the fact that the mAb 1-10 antibody is specific for the N-terminus of the wPTH, and this epitope is altered with the additional methionine residue at the N-terminus of mPTH.

Surface-based assays typically have a linear region where the signal correlates to the target concentration. Using the multiplexed cartridge with the two unique capture antibodies as described in this example, a system of linear equations can be generated to correlate the fluorescence intensities from the different spots to the absolute concentrations within the mixture. The system can be described using Equation 3. In this equation, $F_1$ is indicative of the final reported value for the mAb 15-25 capture antibody spots and $F_2$ is the final reported value for the mAb 1-10 capture antibody spots. The slopes and intercepts can be obtained through the data in FIG. 7.

$$\begin{bmatrix} F_1 \\ F_2 \end{bmatrix} = \begin{bmatrix} m_{1w} & m_{1m} \\ m_{2w} & m_{2m} \end{bmatrix} \cdot \begin{bmatrix} [wPTH] \\ [mPTH] \end{bmatrix} + \begin{bmatrix} b_1 \\ b_2 \end{bmatrix} \quad \text{Equation 3}$$

Once the slopes and intercepts for the system of equations have been identified via calibration, this multiplexed approach on a single cartridge can be used to predict the concentrations of a mixed sample using Equation 4. Note that the $m_{1w}:m_{1m}$ ratio must be significantly different than $m_{2w}:m_{2m}$ ratio to enable the accurate prediction of a mixed sample $$\begin{bmatrix} [wPTH] \\ [mPTH] \end{bmatrix} = \begin{bmatrix} m_{1w} & m_{1m} \\ m_{2w} & m_{2m} \end{bmatrix} \setminus \left( \begin{bmatrix} F_1 \\ F_2 \end{bmatrix} - \begin{bmatrix} b_1 \\ b_2 \end{bmatrix} \right) \quad \text{Equation 4}$$

Figure 8:
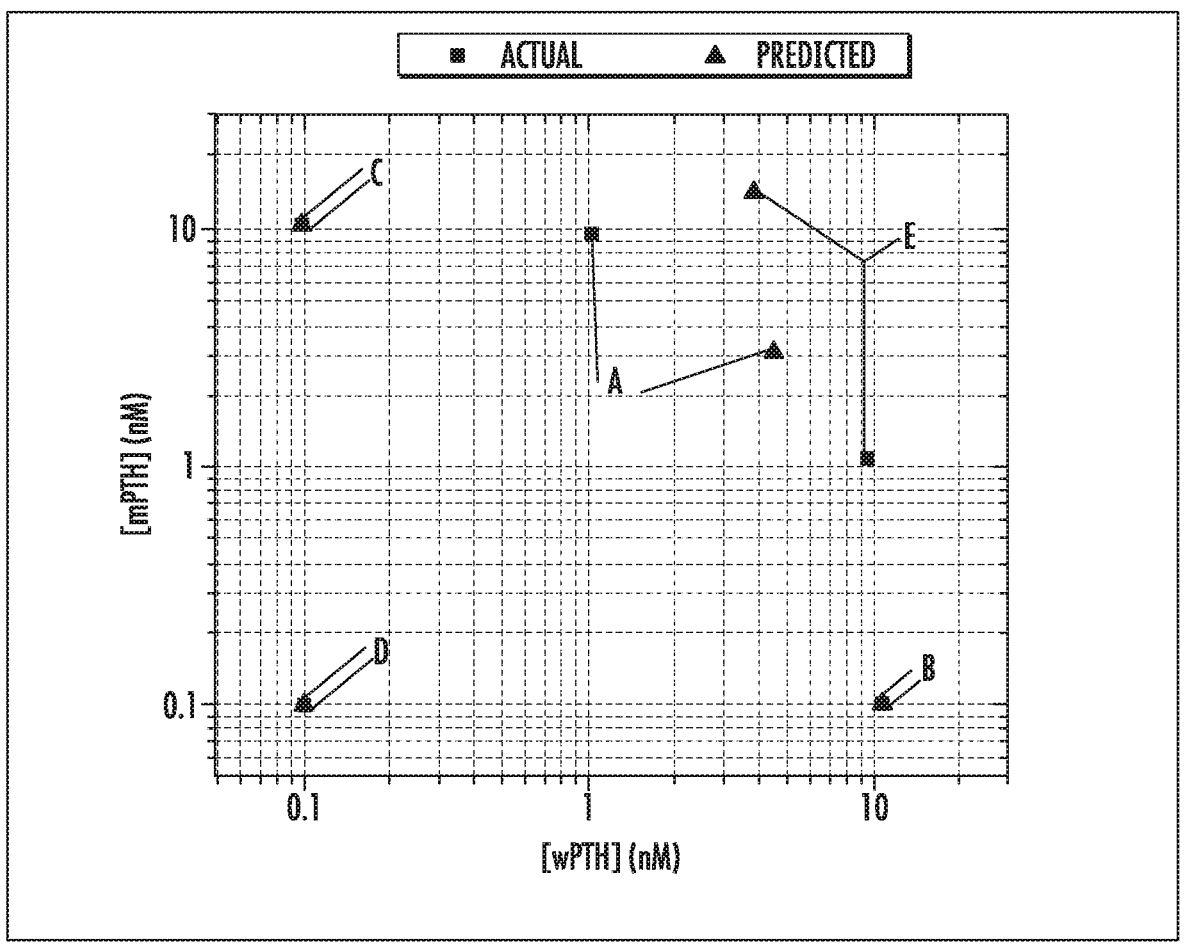
FIG. 8 is a plot showing actual concentrations (squares) and predicted concentrations (triangles) of wPTH and mPTH in mixed samples.

FIG. 8 is an example of the utility of the multiplexed cartridge approach to where a single cartridge can be used to identify the concentrations of related proteins in a mixed sample. Multiple samples were tested using the aforementioned method, and the concentrations of wPTH and mPTH were predicted using the final, reported fluorescence intensities from each cartridge and the associated system of equations. The accuracy of the prediction is indicated by the distance between the triangle and the square for a given set of markers, where shorter distances equate better accuracies. FIG. 8 shows actual concentrations (squares) and predicted concentrations (triangles) of wPTH and mPTH in mixed samples (log-log plot). A indicates a sample with 10 ng/mL wPTH and 90 ng/mL mPTH. B indicates a sample with 100 ng/mL wPTH and 0 ng/mL mPTH. C indicates a sample with 0 ng/mL wPTH and 100 ng/mL mPTH. D indicates a sample with 0 ng/mL wPTH and 0 ng/mL mPTH. E indicates a sample with 90 ng/mL wPTH and 10 ng/mL mPTH.

Instead of passing the different components over the microarray in a sequential manner, the sample could first be mixed with the detection antibody. This mixture of the sample and detection antibody would form complexes and would then be passed over the microarray. In this case, the one or more recognition elements would have different sensitivities for the complexes comprising the detectable moiety and the target and/or variant thereof.

The orientation of these assays could be flipped to where the mAb 53-84 serves as the capture antibody and mAb 15-25 and mAb 1-10 serve as the fluorescently labeled detection antibodies (using a similar approach to Example 1 with multiple cartridges). Further, additional, unique capture Abs could optionally be printed. If done, the signals could be added in Equations 1 and 2 to make them more complex for continued use in predicting the concentrations of wPTH and mPTH and/or for any other desired purpose.

Example 3

Understanding Kinetics of Metabolism and Impact of Complicating Pathological Processes By knowing something about the way the different proteins are produced and cleared from the body, the time-dependent concentrations of each molecule can be described with a set of differential equations that account for the secretion and clearance of the two populations. As an example, with a multiplexed diagnostic assay that can accurately measure the absolute concentrations of wPTH and iPTH at unique points of time, the kinetic rate constants for this model can be generated and used to better understand the status of the individual patient. With a sufficient mathematical description, the experimentally determined rate of secretion of wPTH after the suspect gland is excised can be determined and then compared to the original rate of secretion. This reduction can be attributed to the surgical procedure and could potentially be the basis of an improved criterion of a successful surgery.

All criteria that are currently being used in the clinic are based on the absolute drop in the systemic concentration of PTH detected by the intraoperative assay (detecting both wPTH and iPTH), and they show a range of negative predictive values (42%-88%) and overall accuracies (79-97%) in clinical studies. Through the implementation of the presently disclosed subject matter, a better criterion can be defined that can improve the positive and negative predictive values—as well as the resulting overall accuracy of the diagnostic—based on the drop in the actual PTH secretion rate. In addition, it allows the measurement to be performed sooner. That is, instead of waiting on the clearance of PTH to achieve concentrations that indicate that the rate of secretion has significantly dropped, one can determine the rate of secretion directly in a manner that can be quicker than current approaches.

Figure 9:
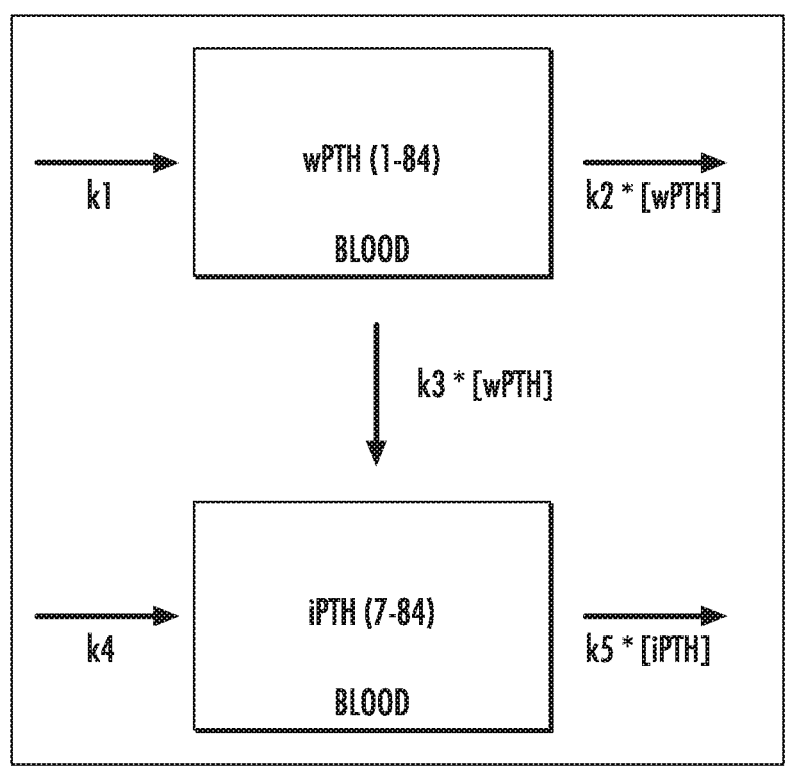
FIG. 9 is a schematic of a mathematical model for wPTH and iPTH.

The changing concentrations of wPTH and iPTH in whole blood can be described with the schematic in FIG. 9 and differential equations (Equation 5 and 6):

$$\frac{\delta wPTH}{\delta t} = k1 - k2[wPTH] - k3[wPTH] \qquad \text{Equation 5}$$

$$\frac{\delta iPTH}{\delta t} = k4 + k3[wPTH] - k5[iPTH] \qquad \text{Equation 6}$$

In these equations, k1 is the rate of secretion of wPTH by the parathyroid glands, k2 is the combined rate of clearance of wPTH by the livers and kidneys and the peripheral metabolism of whole PTH to fragments smaller than iPTH, k3 is the rate of peripheral metabolism of wPTH to iPTH, k4 is the rate of secretion of iPTH by the parathyroid glands, and k5 is the combined rate of clearance of intact PTH by the livers and kidneys as well as the peripheral metabolism to smaller fragments. Note that k1 and k4 are calcium dependent.

The validity of the best-fit kinetic rate constants for this system of differential equations to output meaningful rates was tested with a set of already published data (Nguyen-Yamamoto 2002). In that work, human wPTH (h-wPTH) was administered via a bolus injection to two sets of rats. The rats of one set were healthy. The rats of the other set were nephrectomized but otherwise healthy, preventing them from clearing the through the normal pathway of the kidneys. Because of this, it is expected that the rate of clearance of wPTH and iPTH should be lower in nephrectomized rats than normal rats. Other clearance pathways are expected to continue to perform normally.

Figure 10:
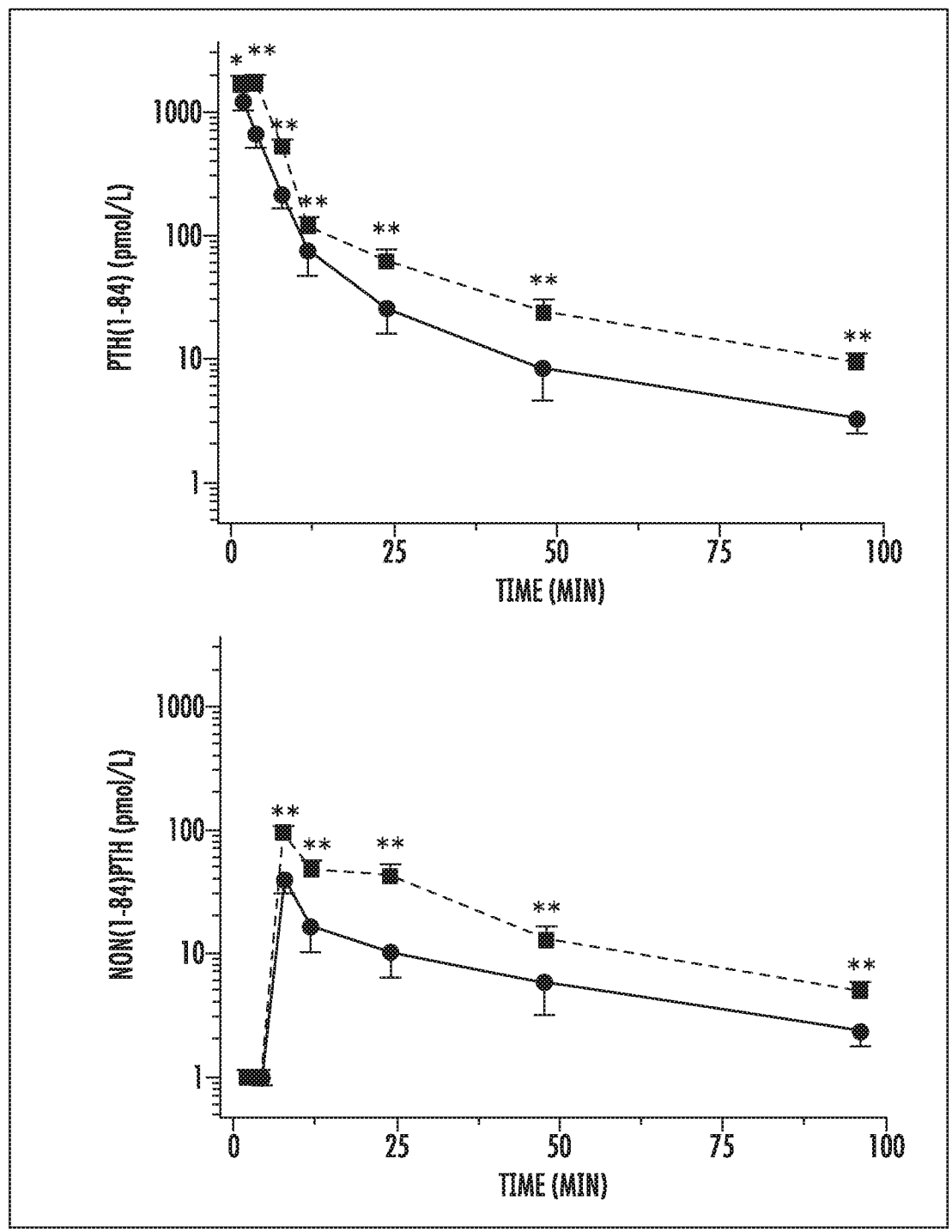
FIG. 10 is a plot showing time-dependent decay of the wPTH (PTH (1-84)) and iPTH (non(1-84) PTH) in normal (solid line) and nephrectomized (dotted line) rats from the combined study using the assays and HPLC (Nguyen-Yamamoto 2002).

After injection of human wPTH, blood draws were performed at various times. These samples were examined via Gen 2 PTH assays that respond to wPTH and iPTH equally, and therefore detect the combined concentration of wPTH and iPTH. These assays do not respond to rat PTH. These samples were also examined with HPLC to determine the relative concentrations of wPTH and iPTH. By pairing the $2^{nd}$ generation assay data with the HPLC data, it is possible to generate the kinetic, decay curves shown below for wPTH and iPTH after injection. PTH (1-84) and non (1-84) PTH are the terms the original authors used for wPTH and iPTH, respectively. Referring to FIG. 10, solid and dotted lines are indicative of the normal and nephrectomized rats, respectively.

Figure 11:
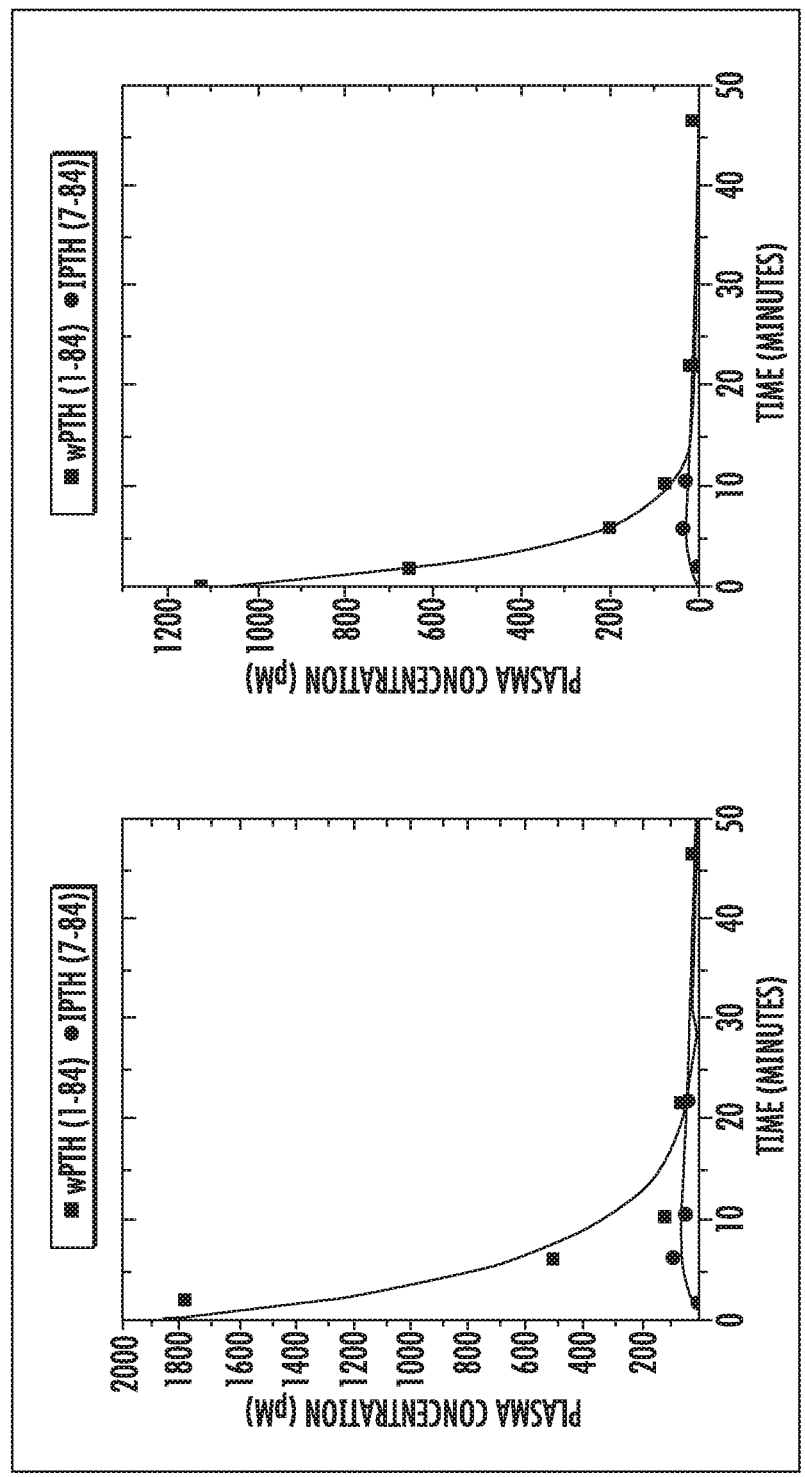
FIG. 11 is a plot of kinetic traces of [wPTH] (squares) and [iPTH] (circles) in response to bolus injection of wPTH in (A) nephrectomized rats and (B) normal rats.

Because rats do not synthesize human wPTH or iPTH, it is possible to describe these systems with the system of differential equations (Equation 1 and 2) and set k1 and k4 to zero. By minimizing the standard error of prediction, the optimal rates for k2, k3, and k5 were identified for the best-fit of the data. After getting a rough estimate of k3, it was fixed because the nephrectomy is not expected to change the peripheral metabolism of wPTH into iPTH. The kinetic data was then fit to identify k2 and k5 in order to examine the effect of the nephrectomy on the clearance of the wPTH and iPTH. This generated the plots in FIG. 11. In FIG. 11, kinetic traces of wPTH and iPTH concentrations in response to bolus injection of wPTH in (A) nephrectomized rats and (B) normal rats are shown. The lines represent the best fit data according to Eq 1 and Eq 2 where the rates for A are: k1=0, k2=0.1616, k3=0.01, k4=0, k5=0.0547, and the rates for B are: k1=0, k2=0.2716, k3=0.01, k4=0, k5=0.0714. The best fit rates are shown together in Table 1.

TABLE 1

Comparison of experimentally determined kinetic rate constants for healthy and nephrectomized rats.
Experimentally determined kinetic rate constants

|    | Normal | Nephrectomized |
|----|--------|----------------|
| k1 | 0      | 0              |
| k2 | 0.2716 | 0.1616         |
| k3 | 0.01   | 0.01           |
| k4 | 0      | 0              |
| k5 | 0.0714 | 0.0547         |

The best-fit k2 and k5 rates—which indicate the clearance of wPTH and iPTH, respectively—are ~25-40% lower for nephrectomized rats than normal rats. This value agrees with what is expected in the physiological case. Nephrectomized rats do not have the ability to clear the related PTH proteins via the normal, kidney pathway. However, they do still have other pathways for the proteins to be cleared (via peripheral metabolism and the liver). In this case, the kinetic rates of clearance clearly show the ability to distinguish non-normal from normal. This experiment validates the capability of being able to use the concentrations of a set of related proteins to better understand a specific physiological system and provide an improved diagnosis.

While obtaining the experimental data originally published in (Nguyen-Yamamoto 2002) required a time-intensive process of purifying a serum sample and then separating it using HPLC to determine the relative concentrations of these two populations, the proposed multiplexed diagnostic test can be used to obtain similar data to that shown in FIG. 10. This type of diagnostic test can either be in a typical bench-top format capable of being used in a core laboratory by technologists or in a more portable format that is capable of being used at the point-of-care.

Using a similar strategy to compare the secretion rates (specifically k1) of PTH before and after a parathyroidectomy is expected to give an even greater change in rates. Because of the high levels of PTH in primary hyperparathyroidism, the normally functioning parathyroid glands are producing negligible amounts of PTH. This means the secretion rates of PTH immediately after a successful parathyroidectomy should be much lower than normal. Prior to the parathyroidectomy, the over-acting glands are already outputting significantly higher values than normal. Therefore, the decrease in the rate of secretion of wPTH upon successful excision of the over-acting gland is expected to be an order of magnitude or more.

In addition, it is possible that k2, k3, and k5 can be predicted for a given patient based on basic measurable factors (such as risk factors, weight, age, kidney function, etc.). By having good predictors of these clearance rates, the secretion rates of wPTH and iPTH (k1 and k4) can be determined with minimal samples and time during a parathyroidectomy. In addition, the secretion rate constants k1 and k4 can potentially be determined for a patient by performing a measurement on the microarray before the parathyroidectomy. In this case, the assumption would need to be made that the system was in steady state.

This type of multiplexed diagnostic can also be implemented to help diagnose whether the hyperparathyroidism is primary, secondary, or tertiary. The kinetics of PTH secretion and clearance can be determined by giving patients a bolus of wPTH and studying the time-dependent changes of wPTH and iPTH back to pre-bolus levels.

Example 4

Parathyroid Aspirate PTH Testing

Prior to a parathyroidectomy, many surgeons perform a needle aspirate on suspected parathyroid glands to determine whether they are parathyroid tissue or a thyroid nodule. While this test is effective at identifying a parathyroid gland, it is a poor predictor of whether that gland is hyperfunctioning due to the multiple variables involved (i.e. how much tissue is removed, how much volume is used to dilute the aspirate).

In primary hyperparathyroidism, the ratio of wPTH secretion rate to iPTH secretion rate is expected to be different in hyperfunctioning tissue compared to normal tissue. As such, it is suspected that the relative concentrations of wPTH to iPTH in the aspirate of these glands should reflect the pathology. A test that can distinguish the concentration of wPTH and iPTH (and/or the relative concentrations) can be used as a clinical determinant of normal vs hyperfunctioning tissue. This test is insensitive to the variables that currently prevent needle aspirates from being a diagnostic tool of hyperfunctioning tissue (i.e. how much tissue is removed, how much volume is used to dilute the aspirate). Therefore, the presently disclosed subject matter provides a determination of pathological function of an individual gland prior to or during surgery and can minimize the surgery time of a parathyroidectomy. This can significantly decrease costs and risks to the patient.

An example procedure is to vigorously syringe ~0.5 mL buffer into excited tissue. Retrieve the buffer and perform a one-step assay (similar to the methods of Examples 1 and 2) with a single, multiplexed cartridge using capture molecules against wPTH and iPTH. The results provide a ratio of wPTH to iPTH. Elevated concentrations can be analyzed in ~3 minutes.

REFERENCES

Bieglmayer, C., G. Prager, et al. (2002). "Kinetic analyses of parathyroid hormone clearance as measured by three rapid immunoassays during parathyroidectomy." Clinical Chemistry 48(10): 1731-1738.

Boudou, P., F. Ibrahim, et al. (2005). "Third- or second-generation parathyroid hormone assays: A remaining debate in the diagnosis of primary hyperparathyroidism." Journal of Clinical Endocrinology and Metabolism 90(12): 6370-6372.

Carneiro, D. M., C. C. Solorzano, et al. (2003). "Comparison of intraoperative iPTH assay (QPTH) criteria in guiding parathyroidectomy: Which criterion is the most accurate?" Surgery 134(6): 973-981.

Caron, P., J. C. Maiza, et al. (2009). "High third generation/second generation PTH ratio in a patient with parathyroid carcinoma: Clinical utility of third generation/second generation PTH ratio in patients with primary hyperparathyroidism." Clinical Endocrinology 70(4): 533-538.

Cavalier, E., D. Betea, et al. (2014). "The third/second generation PTH assay ratio as a marker for parathyroid carcinoma: Evaluation using an automated platform." Journal of Clinical Endocrinology and Metabolism 99(3): E453-E457.

Gao, P. and P. D'Amour (2005). "Evolution of the parathyroid hormone (PTH) assay—Importance of circulating PTH immunoheterogeneity and of its regulation." Clinical Laboratory 51(1-2): 21-29.

Goodman, W. G. (2005). "The evolution of assays for parathyroid hormone." Seminars in Dialysis 18(4): 296-301.

Grant, C S Arch Surg. 2005 May; 140(5):472-8; discussion 478-9. PMID: 15897443

Greene A B. J Am Coll Surg. 2009 September; 209(3):332-43. doi: 10.1016/j.jamcollsurg.2009.05.029. PMID: 19717037

Inabnet W B. World J Surg. 2004 December; 28(12):1212-5. Epub 2004 Nov. 4. Review. PMID:15517480

Irvin G L III, Dembrow V D, Prudhomme D L. Irvin G L 3rd, Dembrow V D, Prudhomme D L. Am J Surg. 1991 October; 162(4):299-302. PMID:168317

Irvin G L III, Dembrow V D, Prudhomme D L. Surgery. 1993 December; 114(6):1019-22; discussion 1022-3. PMID:8256205

Ligler F S, Sapsford K E, Golden J P, Shriver-Lake L C, Taitt C R, Dyer M A Barone S, and Myatt C J. The array biosensor: Portable, automated systems. Anal. Sci. 2007 23:5-10.

Ligler F S, Taitt C R (eds.). Optical Biosensors: Today and Tomorrow Elsevier, The Netherlands, 2008, 700 pp.).

Lochhead M J, Todorof K, Delaney M, et al. Rapid multiplexed immunoassay for simultaneous serodiagnosis of HIV-1 and coinfections. J. Clin. Micro. 2011 October: 3584-3590.

Meneely J P, Campbell K, Greef C, Lochhead M J, Elliott C T. Development and validation of an ultrasensitive fluorescence planar waveguide biosensor for the detection of paralytic shellfish toxins in marine algae. Biosensors Bioelectronics 2012 41:691-697.

Meyer S K, Zorn M, Frank-Raue K, Büchler M W, Nawroth P, Weber T. Clinical impact of two different intraoperative parathyroid hormone assays in primary and renal hyperparathyroidism. Eur J Endocrinol. 2009 February; 160(2): 275-81. doi: 10.1530/EJE-08-0292. Epub 2008 Nov. 12. PMID 19004983.

Nguyen-Yamamoto, L., Rousseau, L., Brossard, J. H., Lepage, R., Gao, P., Cantor, T., D'Amour, P., 2002. Origin of parathyroid hormone (PTH) fragments detected by intact-PTH assays. European Journal of Endocrinology 147(1), 123-131.

Pelleitteri P K Head Neck. 2013 January; 35(1): 123-32. doi: 10.1002/hed.21898. Epub 2011 Oct. 27. Review. PMID: 22034046

Potts, J. T. (2013). "A Short History of Parathyroid Hormone, Its Biological Role, and Pathophysiology of Hormone Excess." Journal of Clinical Densitometry 16(1): 4-7.

Udelsman R. Ann Surg. 2002 May; 235(5):665-70; discussion 670-2. PMID:11981212

Yamashita, H., P. Gao, et al. (2003). "Large carboxy-terminal parathyroid hormone (PTH) fragment with a relatively longer half-life than 1-84 PTH is secreted directly from the parathyroid gland in humans." European Journal of Endocrinology 149(4): 301-306.

It will be understood that various details of the presently disclosed subject matter can be changed without departing from the scope of the presently disclosed subject matter. Furthermore, the foregoing description is for the purpose of illustration only, and not for the purpose of limitation.

What is claimed is:

1. A method for determining concentrations of a target hormone molecule and a variant thereof in a sample, the method comprising:
   providing a sample comprising or suspected to comprise a target hormone molecule and at least one variant thereof, wherein the variant has a different number of amino acids than the target hormone molecule;
   exposing the sample to two or more recognition elements, wherein at least one recognition element binds the target hormone molecule and at least one recognition element binds both the target hormone molecule and the at least one variant, and wherein the two or more recognition elements are spectrally distinguishable;
   detecting a signal associated with the binding of the target hormone molecule to a recognition element in the two or more recognition elements and a signal associated with the binding of the at least one variant to a recognition element in the two or more recognition elements; and
   determining the concentration of the target hormone molecule and the at least one variant thereof based on the signals, provided that determining the concentration of the target hormone molecule and the at least one variant thereof based on the signals can comprise determining that only one of the molecules is present.

2. The method of claim 1, wherein the target hormone molecule and the at least one variant thereof comprise a hormone and one or more fragment(s) thereof.

3. The method of claim 1, wherein the sample comprises a clinical fluid and/or a tissue aspirate.

4. The method of claim 1, wherein the two or more recognition elements each comprise an antibody, a peptide, an aptamer, and/or a combination thereof.

5. The method of claim 1, wherein the two or more recognition elements bind to different epitopes of the target hormone molecule.

6. The method of claim 1, wherein the two or more recognition elements have different sensitivities for the target hormone molecule and the at least one variant thereof.

7. The method of claim 1, wherein the two or more recognition elements have different sensitivities for a complex comprising the target hormone molecule and for a complex comprising the at least one variant thereof.

8. The method of claim 1, wherein the signal associated with the binding of the target hormone molecule to a recognition element in the two or more recognition elements and/or the signal associated with the binding of the at least one variant thereof to a recognition element in the two or more recognition elements is/are compared to a known sensitivity of the recognition element for the target hormone molecule and/or of the recognition element for the at least one variant thereof to predict the concentration of the target hormone molecule and/or the at least one variant thereof within the sample.

9. The method of claim 1, wherein the at least one variant is a metabolic fragment of the target hormone molecule.

10. The method of claim 1, wherein the target hormone molecule is whole parathyroid hormone (wPTH, SEQ ID NO: 1).

11. The method of claim 1, wherein the at least one variant thereof is intact parathyroid hormone (iPTH, SEQ ID NO: 2).

* * * * *